United States Patent [19]

Umetani et al.

[11] Patent Number: 5,115,074

[45] Date of Patent: May 19, 1992

[54] EPOXY COMPOUND, PRECURSOR THEREOF, PRODUCTION PROCESSES THEREOF, USE OF THE PRECURSOR AND CURED PRODUCT OF THE EPOXY COMPOUND

[75] Inventors: Hiroyuki Umetani; Shunichi Matsumura; Takeyoshi Yamada, all of Iwakuni, Japan

[73] Assignee: Teijin Limited, Osaka, Japan

[21] Appl. No.: 623,025

[22] Filed: Dec. 6, 1990

[30] Foreign Application Priority Data

Dec. 6, 1989 [JP] Japan ................................ 1-315362

[51] Int. Cl.$^5$ ............................................. C08G 59/00
[52] U.S. Cl. ....................................... 528/98; 525/450
[58] Field of Search ................... 528/87, 98, 96, 97, 528/99, 100, 101; 525/117, 450, 507, 535, 111.5; 562/425; 549/517, 551, 559, 560

[56] References Cited

U.S. PATENT DOCUMENTS 4,130,549 12/1978 Ueno et al. ............................ 528/93
4,390,664 6/1983 Kanayama ........................... 525/117
4,394,496 7/1983 Schrader ................................ 528/98

FOREIGN PATENT DOCUMENTS 0095609 7/1983 European Pat. Off. .

OTHER PUBLICATIONS

Chemical Abstracts, vol. 108, No. 26, 27, Jun. 1988.
Patent Abstracts of Japan, vol., 10, No. 377, (C-392)(2434), Dec. 16, 1986 and JP A-61167677, Jul. 29, 1986.
Vol. 10, No. 107, (C-341)(2164), Apr. 22, 1986; and A-60237047, Nov. 25, 1985.

Primary Examiner—John Kight, III
Assistant Examiner—Richard L. Jones
Attorney, Agent, or Firm—Sherman and Shalloway

[57] ABSTRACT

There is provided a novolak-type hydroxycarboxylic acid or an ester thereof, an epoxy compound produced therefrom, a composite material comprising a matrix resin of the cured product and a reinforcing material, and a process for the production of the epoxy compound. The epoxy compound produces a cured product having excellent water resistance, heat resistance, chemical resistance, mechanical properties, dimensional stability and electrical properties.

17 Claims, 7 Drawing Sheets

EPOXY COMPOUND, PRECURSOR THEREOF, PRODUCTION PROCESSES THEREOF, USE OF THE PRECURSOR AND CURED PRODUCT OF THE EPOXY COMPOUND

DETAILED DESCRIPTION OF THE INVENTION

This invention relates to a novel epoxy compound, a precursor thereof and processes for the production thereof, and use of the precursor and a cured product of the epoxy compound. More specifically, it relates to an epoxy cured product having excellent water resistance, heat resistance, chemical resistance, mechanical properties, dimensional stability and electrical properties, an epoxy compound to provide the epoxy cured product, a precursor of the epoxy compound, production processes thereof and use of the precursor as an epoxy curing agent.

Conventionally, cured epoxy resins are widely used in fields of coating compositions, electrical insulating materials, civil engineering and construction materials, adhesives, fiber-incorporated reinforced composite materials, and the like due to their various excellent properties. And, the following processes are well known as a practical process for the production of a heat-resistant cured epoxy resin among these cured epoxy resins used in such fields.

1. A process in which tetraglycidyl-methylene-dianiline and diaminodiphenyl sulfone are reacted and cured.
2. A process in which a polyglycidyl ether of phenol novolak and diaminodiphenylsulfone are reacted and cured.
3. A process in which tetraglycidyl-methylene-dianiline and dicyandiamide are reacted and cured, and
4. A process in which a polyglycidyl ether of phenol novolak and dicyandiamide are reacted and cured.

U.S. Pat. No. 4,394,496 discloses a monomeric epoxide of the formula

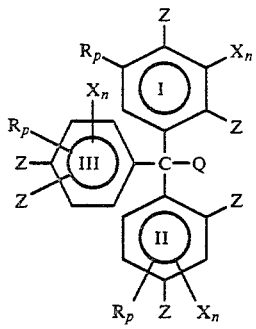

wherein
Q is H or an alkyl group of from 1 to about 10 carbon atoms;
each R independently represents an alkyl group of from 1 to about 12 carbon atoms, a phenyl or cycloalkyl group of from 3 to about 6 carbon atoms; and
each Z independently represents H or

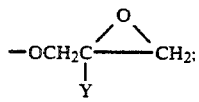

with the proviso that at least one Z on each of Rings I, II and III is

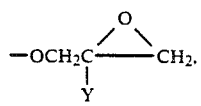

each Y independently represents H or methyl;
each X independently represents bromo, chloro or nitro;
each p independently is 0, 1 or 2,
each n independently is 0, 1 or 2, and the sum of n+p for each ring being 0, 1, 2 or 3 when both Z groups are other than hydrogen.

In the above epoxide, none of the Rings I, II and III do not contain any oxygen-containing group other than the nitro and glycidyl ether groups as is clear from the above definition.

Japanese Laid-Open Patent Publication No. 36205/1980 discloses a process for the production of a high-purity epoxide (whose epoxy equivalent is about 125 to 140) of the following formula,

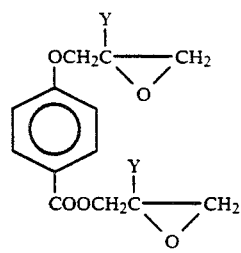

wherein Y is as defined above, which comprises reacting p-hydroxy benzoic acid and epihalohydrin.

The above epoxide has its characteristic features in that it contains a glycidyl ester group in addition to a glycidyl ether group as an oxygen-containing group, as is shown in the above formula.

Said Japanese Laid-Open Patent Publication No. 36205/1980 discloses only usefulness of the above epoxide as a curing agent for a coating composition powder, and discloses nothing concerning the performances of the cured product of the above epoxide. However, the present inventors' study has showed that the cured product of the above epoxide has very high water absorption and when it is immersed in a boiling water, its water resistance decreases with an increase in swelling. The reason therefor is not clear. However, one major reason is believed to be that said epoxide contains, in addition to a glycidyl ether group, a glycidyl ester group as the oxygen-containing hydrophilic groups in the molecule.

Therefore, it is an object of this invention to provide a novel epoxy compound.

It is another object of this invention to provide an epoxy compound which has many oxygen-containing hydrophilic groups such as glycidyl ether and glycidyl ester groups but gives a cured product having excellent water resistance equivalent to that of a cured product of an epoxy compound having a corresponding skeleton structure free from any glycidyl ester group.

It is further another object of this invention to provide an epoxy compound which gives a cured product having not only excellent water resistance but also excellent heat resistance, chemical resistance, mechanical properties, dimensional stability and electrical properties.

It is still another object of this invention to provide a novel hydroxycarboxylic acid and an ester thereof as a precursor of the above epoxy compound.

It is yet another object of this invention to provide industrially advantageous processes for producing the above epoxy compound and precursor of this invention efficiently and economically.

It is further another object of this invention to provide novel use of the above hydroxycarboxylic acid and ester thereof, provided by this invention, as an epoxy curing agent.

Further, it is another object of this invention to provide a cured product having the above-described excellent properties derived from the epoxy compound of this invention.

It is still further another object of this invention to provide a composite material which comprises, as a matrix resin, a cured product derived from the epoxy compound of this invention and has excellent properties.

Other objects and advantages of this invention will be apparent from the following description.

According to this invention, the above objects and advantages of this invention are achieved by a compound of the following formula (II)

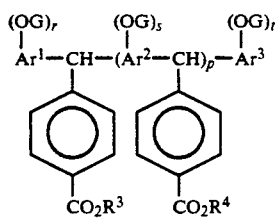

wherein:
Ar$^1$, Ar$^2$ and Ar$^3$ may be same or different and each independently represents a benzene skeleton, a naphthalene skeleton or a skeleton of the formula

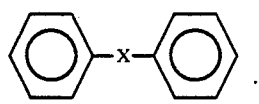

in which X is a bond, —O—, —S—, —SO$_2$—,

or an alkylidene group having 1 to 3 carbon atoms, provided that these skeletons may be substituted with a halogen atom or an alkyl group having 1 to 5 carbon atoms and that the total number of carbon atoms of each of Ar$^1$, Ar$^2$ and Ar$^3$ is not more than 20,

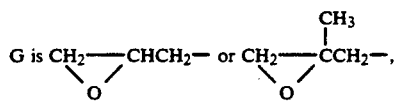

R$^3$ and R$^4$ may be same or different and each independently represents

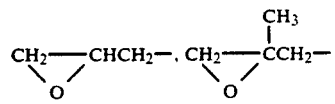

or an alkyl group having 1 to 10 carbon atoms,
p is a number of 0 to 20, and
r, s and t are independently a number of 1 to 3.

Figure 1:
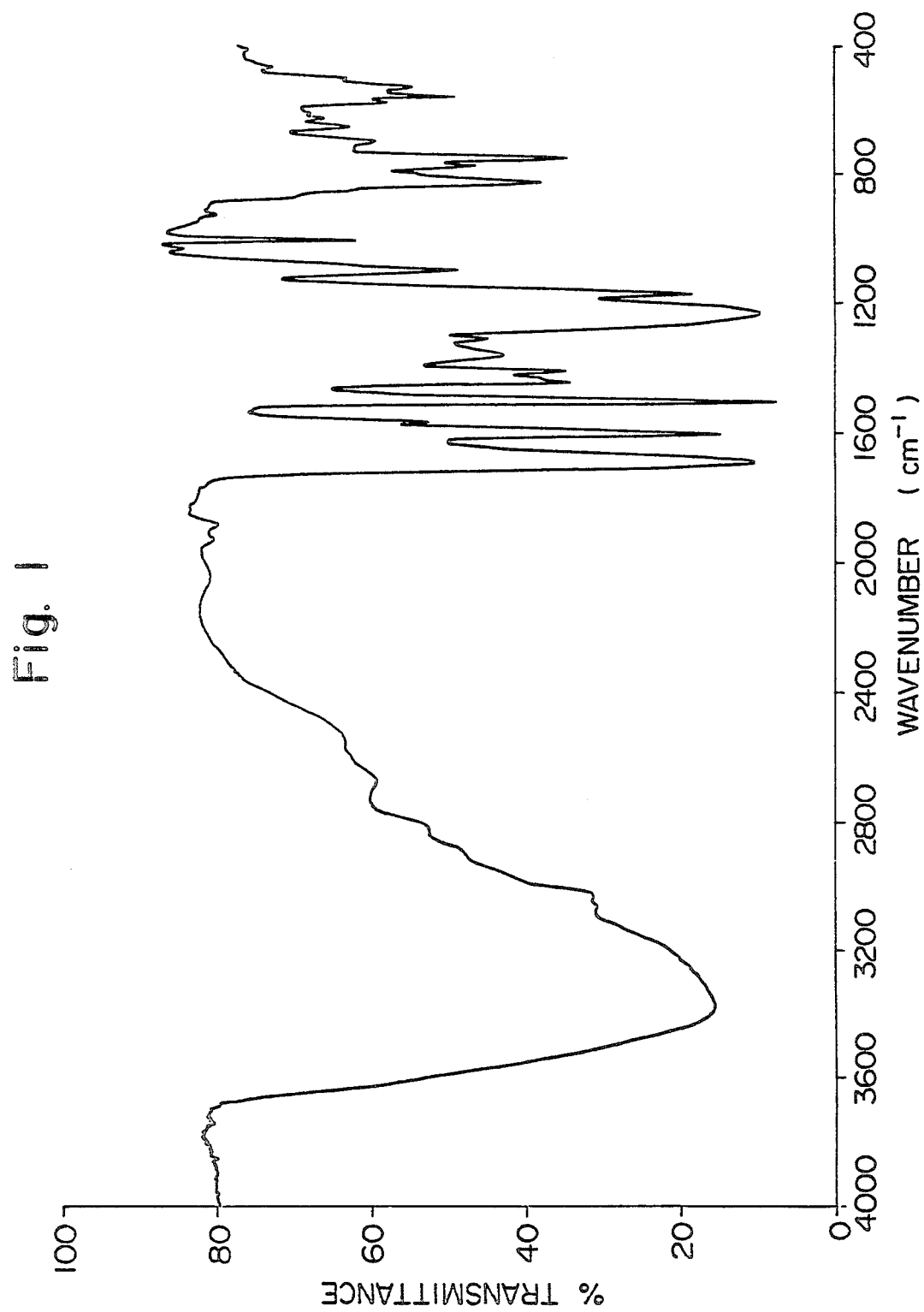
FIG. 1 shows an infrared absorption spectrum of a hydroxycarboxylic acid obtained in Example 1, (1).

In the formula (II), Ar$^1$, Ar$^2$ and Ar$^3$ may be same or different and each independently represents a benzene skeleton, a naphthalene skeleton or a skeleton of the formula

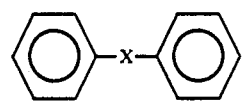

in which X is a bond, —O—, —S—, —SO$_2$—,

or an an alkylidene group having 1 to 3 carbon atoms.

As is clear from the formula (II), Ar$^1$ bonds to (OG)$_r$ and one CH, Ar$^3$ bonds to (OG)$_t$ and one CH, and Ar$^2$ bonds to (OG)$_s$ and two CH's.

It is therefore noted that when these Ar$^1$, Ar$^2$ and Ar$^3$ have no other substituent except for OG and CH('s), Ar$^1$ represents a skeleton having a valence of (1+r), Ar$^3$ shows a skeleton having a valence of (1+t) and Ar$^2$ shows a skeleton having a valence of (2+s). Similarly, it is also noted that when these skeletons further have other substituent(s), the valances thereof increase by a number equivalent to the valence of the other substituent(s). For example, when Ar$^1$ bonds to one OG group (r=1) and a CH group, Ar$^1$ represents a skeleton having a valance of 2, and when the Ar$^1$ is further substituted with one other substituent, the Ar$^1$ represents a skeleton having a valence of 3.

Examples of the skeletons represented by Ar$^1$, Ar$^2$ and Ar$^3$ are

-continued

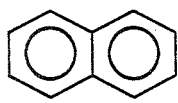

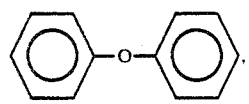

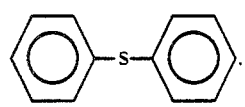

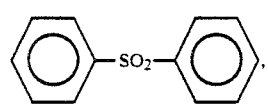

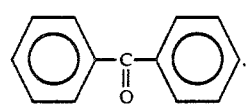

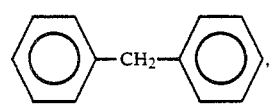

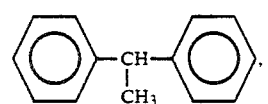

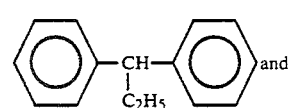 and

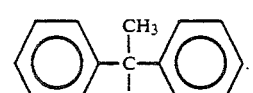

As other substituent(s) substitutable on $Ar^1$, $Ar^2$ and $Ar^3$, there are halogen atoms and an alkyl group having 1 to 5 carbon atoms. Examples of the halogen atoms are fluorine, chlorine, bromine and iodine. The alkyl group having 1 to 5 carbon atoms may be linear or branched, and examples thereof are methyl, ethyl, n-propyl, isopropyl, n-butyl, sec-butyl, iso-butyl, tert-butyl and n-pentyl.

When the "other" substituent(s) is an alkyl group having 1 to 5 carbon atoms, the total number of carbon atoms of the skeleton including such a substituent is twenty at maximum. For example, three n-pentyl groups (each having 5 carbon atoms) are substituted on a benzene skeleton (having 6 carbon atoms), the total number of carbon atoms of the skeleton including the substituents is twenty-one (21), and such a case is therefore excluded from the scope of this invention.

That is, examples of the benzene and naphthalene skeletons represented by $Ar^1$, $Ar^2$ and $Ar^3$ on which such "other" substituent(s) is substituted are a monomethylbenzene skeleton, a dimethylbenzene skeleton, a monochlorobenzene skeleton, a dichlorobenzene skeleton, a monochloromonomethylbenzene skeleton, a monochloronaphthalene skeleton, a monobromobenzene skeleton, a dibromobenzene skeleton, tribromobenzene skeleton, a tetrabromobenzene skeleton (only in the case of $Ar^1$ and $Ar^3$), and a monobromonaphthalene skeleton.

Preferred as $Ar^1$, $Ar^2$ and $Ar^3$ are, for example, a benzene skeleton, a monomethylbenzene skeleton, a naphthalene skeleton, a monochlorobenzene skeleton, a dichlorobenzene skeleton, a monobromobenzene skeleton and a dibromobenzene skeleton. Particularly preferred among these are a benzene skeleton, a monomethylbenzene skeleton, a naphthalene skeleton and a dibromobenzene skeleton.

In the formula (II),

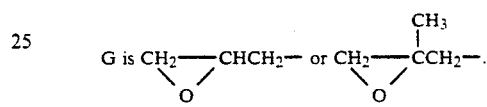

$R^3$ and $R^4$ may be same or different and each independently represents

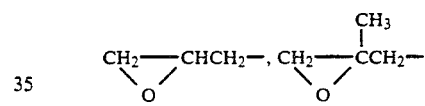

or an alkyl group having 1 to 10 carbon atoms.

The alkyl group having 1 to 10 carbon atoms may be linear or branched, and examples thereof are methyl, ethyl, n-propyl, butyl, pentyl, hexyl, heptyl, octyl, nonyl and decyl groups.

Preferred as $R^3$ and $R^4$ are

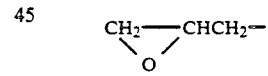

and methyl.

p is a number of 0 to 20, preferably of 0 to 5. When p exceeds 1, plural $Ar^2$'s, plural $R^4$'s and plural G's may be respectively identical or different.

r, s and t may be same or different and each independently represents a number of 1 to 3. When r, s and t are numbers of not less than 2, plural G's in each case may be identical or different.

In the formula (II), corresponding to the above preferred examples of $Ar^1$ and $Ar^3$, specific examples of $(OG)_r$—$Ar^1$— and $(OG)_t$—$Ar^3$— are preferably monoglycidyloxyphenyl (G=

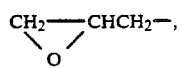

r=1, $Ar^1$=divalent benzene skeleton), di(glycidyloxy)phenyl (G=

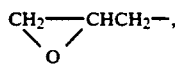

r=2, Ar$^1$=trivalent benzene skeleton), monoglycidyloxymonomethylphenyl

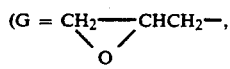

r=1, Ar$^1$=trivalent benzene skeleton monosubstituted with a methyl group), monoglycidyloxynaphthyl

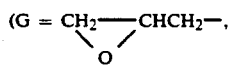

r=1, Ar$^1$=divalent naphthalene skeleton), monochloromonoglycidyloxyphenyl

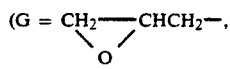

r=1, Ar$^1$=trivalent benzene skeleton monosubstituted with a chlorine atom), dichloromonoglycidyloxyphenyl (G=

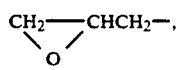

r=1, Ar$^1$=tetravalent benzene skeleton disubstituted with chlorine atoms), monobromomonoglycidyloxyphenyl

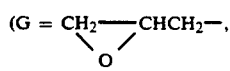

r=1, Ar$^1$=trivalent benzene skeleton monosubstituted with a bromine atom), and dibromomonoglycidyloxyphenyl (G=

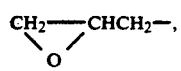

r=1, Ar$^1$=tetravalent benzene skeleton disubstituted with bromine atoms).

Similarly, corresponding to the above preferred examples of Ar$^2$, specific examples of (OG)$_s$—Ar$^2$< are preferably monoglycidyloxyphenylene

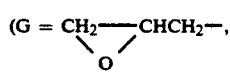

s=1, Ar$^3$=trivalent benzene skeleton), di(glycidyloxy)-phenylene

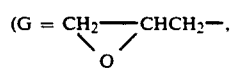

s=1, Ar$^2$=tetravalent benzene skeleton), monoglycidyloxymonomethylphenylene

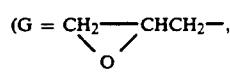

s=1, Ar$^2$=tetravalent benzene skeleton monosubstituted with a methyl group), monoglycidyloxynaphthylene

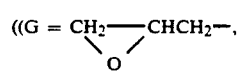

s=1, Ar$^2$=trivarent naphthalene skeleton), monochloromonoglycidyloxy-phenylene

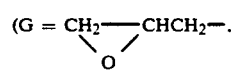

s=1, Ar$^2$=tetravalent benzene skeleton monosubstituted with a chlorine atom), dichloromonoglycidyloxyphenylene

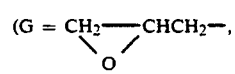

s=1, Ar$^2$=pentavalent benzene skeleton substituted with disubstituted with chlorine atoms), monobromomonoglycidyloxyphenylene

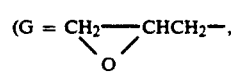

s=1, Ar$^2$=tetravalent benzene skeleton monosubstituted with a bromine atom), and dibromomonoglycidyloxyphenylene

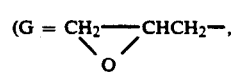

s=1, Ar$^2$=pentavalent benzene skeleton disubstituted with bromine atoms).

It is believed that specific examples of the compound of the formula (II) are clear on the basis of the above explanation. Some of such examples are as follows.

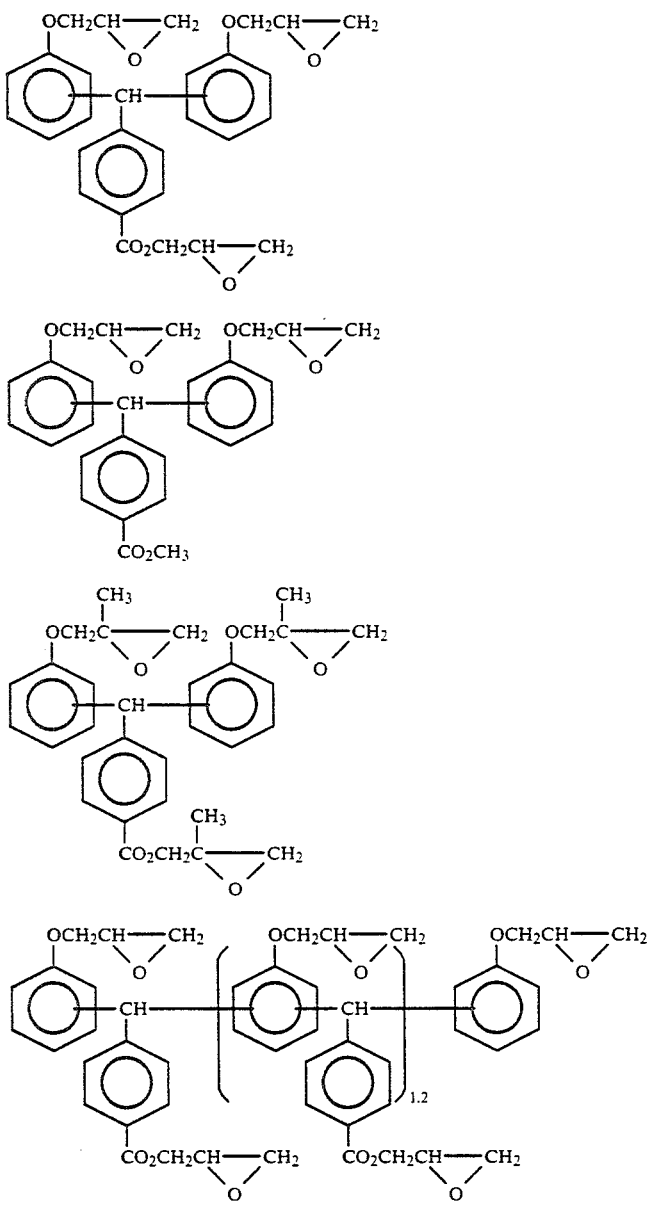

According to this invention, the above epoxy compound of this invention is produced by a process which comprises reacting a compound selected from the group consisting of hydroxycarboxylic acids and esters thereof of the following formula (I)

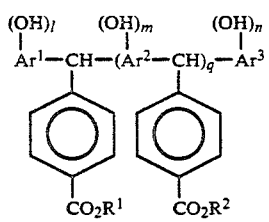

wherein $Ar^1$, $Ar^2$ and $Ar^3$ are as defined in the formula (II), $R^1$ and $R^2$ may be same or different and each independently represents a hydrogen atom or an alkyl group having 1 to 10 carbon atoms, q is a number of 0 to 20, and l, m and n are a number of 1 to 3, with a halohydrin selected from epihalohydrins and β-methylepihalohydrins, (i) at one step in the presence of a basic compound, or (ii) first in the presence of a quaternary ammonium salt and then in the presence of a basic compound.

The compound of the above formula (I) is novel. Therefore, this invention proposes the compound of the formula (I) as well as the compound of the formula (II).

It is to be noted that the explanation of the definition of $Ar^1$, $Ar^2$ and $Ar^3$ in the formula (II) can be applied to the definition of $Ar^1$, $Ar^2$ and $Ar^3$ in the formula (I) as well.

In the formula (I), $R^1$ and $R^2$ may be same or different and each independently represents a hydrogen atom or an alkyl group having 1 to 10 carbon atoms. Examples of the alkyl group having 1 to 10 carbon atoms are the same as those specified with regard to the formula (II). Preferred as $R^1$ and $R^2$ are a hydrogen atom and a methyl group.

q is a number of 0 to 20, preferably of 0 to 5. When q exceeds 1, plural $Ar^2$'s and plural $R^2$'s may be respectively identical or different. l, m and n may be same or different and each independently represents a number of 1 to 3.

In the above formula (I), specific examples of $(OH)_l$—$Ar^1$ and $(OH)_n$—$Ar^3$— are preferably monohydroxyphenyl (l=1, $Ar^1$=divalent benzene skeleton), dihydroxyphenyl (l=2, $Ar^1$=trivalent benzene skeleton), monohydroxymonomethylphenyl (l=1, $Ar^1$=trivalent benzene skeleton monosubstituted with a methyl group), monohydroxynaphthyl (l=1, $Ar^1$=divalent naphthalene skeleton), monochloromonohydroxyphenyl (l=1, $Ar^1$=trivalent benzene skeleton monosubstituted with a chlorine atom), dichloromonohydroxyphenyl (l=1, $Ar^1$=tetravalent benzene skeleton disubstituted with chlorine atoms), monobromomonohydroxyphenyl (l=1, $Ar^1$=trivalent benzene skeleton monosubstituted with a bromine atom), and dibromomonohydroxyphenyl (l=1, $Ar^1$=tetravalent benzene skeleton disubstituted with bromine atoms).

Similarly, examples of $(OH)_m Ar^2<$ are preferably monohydroxyphenylene (m=1, $Ar^2$=trivalent benzene skeleton), dihydroxyphenylene (m=2, $Ar^2$=tetravalent benzene ring), monohydroxymonomethylphenylene (m=1, $Ar^2$=tetravalent benzene skeleton monosubstituted with a methyl group), monohydroxynaphthylene (m=1, $Ar^2$=trivalent naphthalene skeleton), monochloromonohydroxyphenylen (m=1, $Ar^2$=tetravalent benzene skeleton monosubstituted with a chlorine atom), dichloromonohydroxyphenylene (m=1, $Ar^2$=pentavalent benzene skeleton disubstituted with chlorine atoms), monobromomonohydroxyphenylene (m=1, $Ar^2$=tetravalent benzene skeleton monosubstituted with a bromine atom) and dibromomonohydroxyphenylene (m=1, $Ar^2$=pentavalent benzene skeleton disubstituted with bromine atoms).

It is believed that specific examples of the compound of the formula (I) are clear on the basis of the above explanation. Some of such examples are as follows.

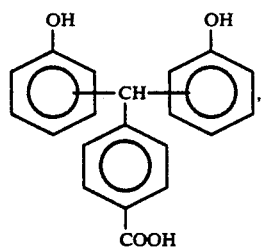

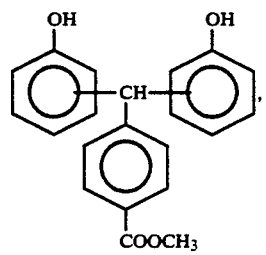

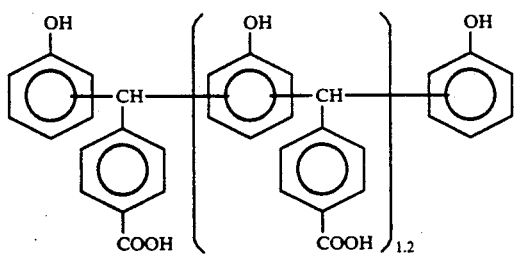

The compound of the formula (I) is a hydroxycarboxylic acid when $R^1$ and $R^2$ are hydrogen atoms, and it is a hydroxycarboxylate ester when at least one of $R^1$ and $R^2$ is an alkyl group.

In the above process of this invention, the compound of the formula (I) and a halohydrin are reacted with each other as described above.

As a halohydrin, any one of epihalohydrins and β-methylepihalohydrins is usable.

Examples of the halohydrin are preferably epichlorohydrin, epibromohydrin, β-methylepichlorohydrin, and β-methylepibromohydrin. Of these, epichlorohydrin and β-methylepichlorohydrin are particularly preferred. These halohydrins may be used alone or in combination. The amount of the halohydrin for use is usually at least 2 mols, preferably at least 3 mols, particularly preferably at least 5 mols, based on one equivalent weight of hydroxyl and carboxyl groups, in total, of the compound of the formula (I).

The hydroxycarboxylic acid or its ester of the formula (I) and the halohydrin are reacted (i) at one step in the presence of a basic compound, or (ii) first in the presence of a quaternary ammonium salt and then in the presence of a basic compound.

Examples of the basic compound for use in the above process (i) are preferably alkali metals such as sodium and potassium, hydroxides thereof, carbonates thereof and bicarbonates thereof. Above all, sodium hydroxide is particularly preferred.

The amount of such a basic compound for use based on one equivalent weight of hydroxyl and carboxyl groups, in total, of the compound of the formula (I) in total is usually at least 0.8 equivalent weight, preferably 0.9 to 3.5 equivalent weight, particularly preferably 1 to 3 equivalent weight.

The reaction above is carried out usually at a temperature between 30° C. and 150° C., preferably between 50° C. and 130° C., particularly preferably between 60° C. and 120° C. The reaction time is usually 1 to 20 hours.

In the above process (ii), the reaction is carried out first in the presence of a quaternary ammonium salt.

Examples of the quaternary ammonium salt are preferably tetraalkyl- or benzyltrialkylammonium salts such as tetramethylammonium chloride, tetraethylammonium chloride, benzyltrimethylammonium chloride and benzyltrimethylammonium acetate. The amount of the quaternary ammonium salt for use based on one equivalent weight of hydroxyl and carboxyl groups, in total, of the compound of the formula (I) is preferably 0.001 to 0.1 mol. For the reaction temperature and reaction time in this case, those conditions specified concerning the above process (i) can be also employed.

After the reaction at the first step, a basic compound is added to the reaction system to carry out the reaction at the second step. The above-specified basic compound at this second step. For the reaction temperature and reaction time at this second step, those conditions specified concerning the above process (i) can be also employed.

The reaction product obtained in the above process (i) or (ii) is usually subjected to post treatment in which unreacted epihalohydrin or β-methylepihalohydrin is removed from the reaction mixture by distillation, and optionally, the remainder is dissolved in a solvent incompatible with water such as toluene, benzene, or the like and then a water-soluble inorganic substance is removed by extraction with water or by filtration.

The epoxy compound of the formula (II) can be produced as described above according to this invention. The resultant epoxy compound is optionally dissolved in an organic solvent such as methyl butyl ketone, benzene or toluene, and further subjected to heat treatment in the presence of a basic compound, e.g. at a temperature between 60° C. and 100° C. for 1 to 20 hours. The amount of the basic compound for use in this treatment is preferably not more than 0.6 equivalent weight, particularly preferably 0.2 to 0.5 equivalent weight, based on one equivalent weight of hydroxyl and carboxyl groups, in total, of the compound of the formula (I). Thus, the epoxy compound can be obtained as a product whose halogen content as impurities is further reduced.

The novel compound of the formula (I) which is used as a starting material in the process of this invention and which also constitutes part of this invention can be produced in the following process according to this invention. This process also constitutes part of this invention.

That is, the compound of the formula (I) can be produced by a process which comprises subjecting to a dehydration and condensation reaction an aldehyde compound of the formula (III)

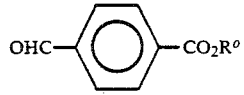
(III)

wherein $R^o$ is a hydrogen atom or an alkyl group having 1 to 10 carbon atoms and an aromatic hydroxy compound of the formula (IV)

$$Ar^o-(OH)_u \quad (IV)$$

wherein $Ar^o$ is a benzene skeleton, a naphthalene skeleton or a skeleton of the formula

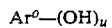

in which
X is a bond, —O—, —S—, —SO₂,

or an alkylidene group having 1 to 3 carbon atoms, provided that these skeletons may be substituted with a halogen atom or an alkyl group having 1 to 5 carbon atoms and that the total number of carbons of $Ar^o$ is not more than 20, and u is a number of 1 to 3, in the presence of an acidic catalyst, and optionally, then subjecting the reaction product to a hydrolysis reaction.

In the formula (III), $R^o$ is a hydrogen atom or an alkyl group having 1 to 10 carbon atoms.

Examples of the alkyl group having 1 to 10 carbon atoms are the same as those specified concerning $R^3$ and $R^4$ in the formula (II). Preferred as $R^o$ are a hydrogen atom and methyl, ethyl and propyl groups.

Examples of the aldehyde compound of the formula (III) are preferably p-formylbenzoic acid, methyl p-formylbenzoate, ethyl p-formylbenzoate and propyl p-formylbenzoate. Of these, p-formylbenzoic acid and methyl p-formylbenzoate are particularly preferred.

The above aldehyde compounds may be used alone or in combination.

The aromatic hydroxy compound, as the other starting material, which is reacted with the above aldehyde compound is represented by the above formula (IV).

In the formula (IV), $Ar^o$ is a benzene skeleton, a naphthalene skeleton or a skeleton of the following formula

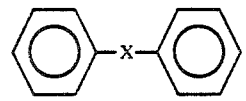

In the above formula, X is a bond, —O—, —S—, —SO₂,

or an alkylidene group having 1 to 3 carbon atoms. And, these skeletons may be substituted with a halogen atom or an alkyl group having 1 to 5 carbon atoms, provided that the total number of carbons of $Ar^o$ is not more than 20.

The explanation of the definition of $Ar^1$, $Ar^2$ and $Ar^3$ in the formula (II) can be applied to the definition of the above $Ar^o$ as well. u is a number of 1 to 3.

Examples of the aromatic hydroxy compound of the formula (IV) are monohydroxyphenolic compounds (u=1) such as phenol, cresol, xylenol, α-naphthol, β-naphthol, bromophenol, chlorophenol, dibromophenol, dichlorophenol, tribromophenol and trichlorophenol; dihydroxyphenolic compounds (u=2) such as resorcinol, dihydroxynaphthalene, bromoresorcinol, chlororesorcinol, dibromoresorcinol, dichlororesorcinol, tribromoresorcinol and trichlororesorcinol; and trihydroxyphenolic compounds (u=3) such as trihydroxybenzene.

Of these compounds, preferred are phenol, cresol, α-naphthol, β-naphthol, bromophenol, 2,6-dibromophenol and resorcinol.

The above aromatic hydroxy compounds may be used alone or in combination.

The aldehyde compound and the aromatic hydroxy compound are subjected to a dehydration and condensation reaction in the presence of an acidic catalyst.

The aldehyde compound and the aromatic hydroxy compound are usually used in such a ratio that the amount of the aromatic hydroxy compound is 0.5 to 2 mole per mole of the aldehyde compound. This ratio can be suitably varied depending upon the polymerization degree q of an intended compound, ie. the compound of the formula (I).

Examples of the acidic catalyst are protonic acids such as nitric acid, sulfuric acid, hydrochloric acid, phosphoric acid, methanesulfonic acid, toluenesulfonic acid and oxalic acid; and Lewis acids such as boron trifluoride, boron trifluoride ether complex, aluminum chloride, tin chloride, zinc chloride, iron chloride and titanium chloride.

Of these, protonic acids are preferred, and in particular, hydrochloric acid, boric acid, methanesulfonic acid and toluenesulfonic acid are preferred.

The amount of the acidic catalyst for use is preferably 0.001 to 0.05 mol per mole of the aldehyde compound. The above acidic catalysts may be used alone or in combination.

The reaction is preferably carried out at a temperature between 80° C. and 250° C. Further, the reaction is advantageously carried out by setting the reaction temperature between 80° C. and 150° C. at the initial stage and gradually increasing the reaction temperature to a desired range.

The reaction time is 1 to 24 hours.

A reaction solvent may be used for the reaction, and an excess amount of the aromatic hydroxy compound may be optionally used so that the aromatic hydroxy compound itself can function as a reaction solvent. Examples of the reaction solvent are preferably aromatic hydrocarbons such as toluene, chlorobenzene, dichlorobenzene, nitrobenzene and diphenyl ether; and ethers such as ethylene glycol dimethyl ether and diethylene glycol dimethyl ether.

According to the above process, in the case of use of an aldehyde compound of the formula (III) in which $R^o$ is a hydrogen atom, there is obtained a hydroxycarboxylic acid of the formula (I) in which $R^1$ and $R^2$ are hydrogen atoms.

Further, in the case of use of an aldehyde compound of the formula (III) in which $R^o$ is an alkyl group having 1 to 10 carbon atoms, there is obtained an ester of a hydroxycarboxylic acid of the formula (I) in which $R^1$ and $R^2$ are corresponding alkyl groups of a hydroxycarboxylate ester in which part of the ester groups are converted to carboxyl groups under hydrolysis.

Such an ester may be optionally subjected to a hydrolysis reaction according to the process of this invention, whereby a hydroxycarboxylic acid formed by converting the ester group to a carboxyl group can be obtained. The hydrolysis can be carried out according to a known method optionally in the presence of an acid or alkali.

As is clear from the above explanation, according to this invention, there is provided a process for the production of the epoxy compound of this invention, which comprises producing the hydroxycarboxylic acid or its ester of the formula (I) from the aldehyde compound of the formula (III) and the aromatic hydroxy compound of the formula (IV), and further reacting the reaction product with a halohydrin.

The present inventors have further made a study of such a process of this invention and succeeded in development of an industrially advantageous production process, which is also proposed here as a process of this invention.

That is, the above-mentioned process of this invention comprises the following three steps:

(1) a step of subjecting an aldehyde compound of the formula (III)-1

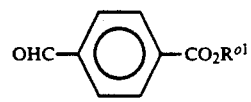

(III)-1 wherein $R^{o1}$ is an alkyl group having 1 to 10 carbon atoms, and an aromatic hydroxy compound of the formula (IV) to a hydration and condensation reaction in the presence of an acidic catalyst, (2) a step of subjecting the resultant reaction mixture to a hydrolysis reaction in the presence of a basic compound, and (3) a step of adding a halohydrin selected from epihalohydrins and β-methylepihalohydrins to the resultant hydrolysis reaction mixture to react a hydrolysis reaction product in said mixture with the halohydrin.

The aldehyde compound of the formula (III)-1 to be used in the step (1) corresponds to the aldehyde compound of the formula (III) in which $R^o$ is an alkyl group having 1 to 10 carbon atoms.

The aromatic hydroxy compound of the formula (IV) is also usable as the other starting material.

For the acidic catalyst and the dehydration reaction conditions, there may be employed the same acidic catalysts and conditions as those in the above process for the production of the hydroxycarboxylic acid and an ester thereof.

Then, in the step (2), the reaction mixture obtained in the step (1) is subjected to a hydrolysis reaction in the presence of a basic compound without isolating a formed hydroxycarboxylate ester from said reaction mixture.

For the basic compound and the amount thereof for use, there may be employed the same basic compounds and amounts as those specified with regard to the variant (i) of the present process for the production of the epoxy compound of this invention.

The hydrolysis reaction is carried out at a temperature preferably between 30° C. and 150° C., more preferably between 50° C. and 130° C., particularly preferably between 60° C. and 120° C. The hydrolysis reaction time is about 20 minutes to about 20 hours.

In addition, it is advantageous to remove an unreacted aldehyde compound and aromatic hydroxy compound from the reaction mixture obtained in the step (i) prior to performance of the step (2), for example, by distillation under reduced pressure and to preliminarily add a basic compound in order to deactivate the acidic catalyst.

Further, in the step (3), a halohydrin is added to the hydrolysis reaction mixture obtained in the step (2) without isolating the formed hydroxycarboxylic acid from said hydrolysis reaction mixture, thereby to react the hydrolysis reaction product with the halohydrin.

Examples of the halohydrin are the same as those specified concerning the process for the production of the epoxy compound of this invention. The amount of the halohydrin for use is preferably at least 2 mols, more preferably at least 3 mols, particularly preferably 5 mols, based on one equivalent weight of carboxyl and hydroxyl groups, in total, of the hydroxycarboxylic acid fully expected to be present in the hydrolysis reaction mixture. The reaction is usually carried out at a temperature between 30° C. and 150° C., preferably at a temperature between 40° C. and 130° C., particularly preferably at a temperature between 50° C. and 120° C.

The reaction time varies depending on a reaction temperature and a stirring state, and is usually 1 to 48 hours. The reaction system is a heterogeneous system formed of a water phase and a halohydrin phase, and it is therefore advantageous to carry out the reaction in the presence of a phase transfer catalyst such as quaternary ammonium salt or a crown ether.

The epoxy compound can be isolated from the so-formed reaction mixture in the same way as in the foregoing process of this invention for the production of the epoxy compound of this invention.

Furthermore, the present inventors have found that the hydroxycarboxylic acid or its ester of the formula (I) can be also used as a curing agent for an epoxy compound in addition to use of as a starting material for the production of the epoxy compound of the formula (II) provided by this invention.

That is, the epoxy curing agent of this invention comprises the hydroxycarboxylic acid or its ester of the formula (I).

The preferably epoxy compound for which the epoxy curing agent of this invention is advantageously usable is a polyepoxy compound having at least two epoxy groups in the molecule, and examples thereof are as follows.

1) Glycidyl ether-type compounds

Aromatic polyols such as 2,2-bis(4-hydroxyphenyl)-propane (bisphenol A), 4,4'-dihydroxydiphenylmethane, 4,4'-dihydroxydiphenylsulfone, resorcinol, phenol novolak, cresol novolak, resorcinol novolak, naphthol novolak, dihydroxynaphthalene novolak; polyols obtained by a dehydration reaction between an aromatic hydroxy compound such as phenol, dihydroxybenzene, naphthol, dihydroxynaphthalene, or the like and an aldehyde such as glyoxal, glutaraldehyde, p-hydroxybenzaldehyde, benzaldehyde, or the like, e.g. in the presence of an acidic catalyst; glycidyl ethers of polyols such as polyhydric alcohols, i.e. butanediol, polypropylene glycol, polyethylene glycol, glycerol, etc., and precursor polymers thereof.

2) Glycidyl ester-type compounds

Glycidyl esters of dicarboxylic acids such as phthalic acid, isophthalic acid, tetrahydrophthalic acid, naphthalenedicarboxylic acid, etc., and precursor polymers thereof.

3) N-Glycidyl-type compounds

Compounds formed by substituting a glycidyl group for active hydrogen bonded to a nitrogen atom of nitrogen-containing compounds such as aniline, isocyanuric acid, methylenedianiline, etc.

4) Glycidyl ether ester-type compounds

Glycidyl ether esters of hydroxycarboxylic acids such as p-hydroxybenzoic acid, hydroxynaphthoic acid, etc.

5) Others

Epoxy resins obtained from alicyclic compounds such as cyclopentadiene, dicyclopentadiene, etc., a triglycidyl compound of p-aminophenol, vinylcyclohexenedioxide, etc.

Of the above polyepoxy compounds, preferred in view of availability and heat resistance of a thermosetting resin to be formed are diglycidyl ether of 2,2-bis(4-hydroxyphenyl)propane (bisphenol A), diglycidyl ether of 4,4'-dihydroxydiphenylmethane, polyglycidyl ether of phenol novolak, polyglycidyl ether of naphthol novolak, polyglycidyl ether of a polyol obtained by a dehydration reaction between phenol and glyoxal, glutaraldehyde, benzaldehyde or p-hydroxybenzaldehyde in the presence of an acidic catalyst, diglycidyl ether of polypropylene glycol, diglycidyl ether of polyethylene glycol, diglycidyl ether of butanediol, diglycidyl ether of glycerol, triglycidyl ether of glycerol, N,N,N',N'-tetraglycidylmethylenedianiline, diglycidyl ether ester of p-hydroxybenzoic acid, diglycidyl ether ester of 2-hydroxy-6-naphthoic acid, a triglycidyl compound of p-aminophenol and vinylcyclohexene dioxide. Particularly preferred are diglycidyl ether of bisphenol A, polyglycidyl ether of phenol novolak, polyglycidyl ether of α-naphthol novolak, polyglycidyl ether of a polyol obtained by a dehydration reaction between phenol and glyoxal, glutaraldehyde, benzaldehyde or p-hydroxybenzaldehyde in the presence of an acidic catalyst, diglycidyl ether of polypropylene glycol, diglycidyl ether of polyethylene glycol, diglycidyl ether of butanediol, diglycidyl ether of glycerol, triglycidyl ether of glycerol, N,N,N',N'-tetraglycidylmethylenedianiline, a triglycidyl compound of p-aminophenol and vinylcyclohexenedioxide. These compounds may be used alone or in combination.

A resin composition comprising the epoxy curing agent of this invention may, as required, additionally contain another curing agent, a cure promoter, a filler, etc. In particular, the cure promoter can further improves the low-temperature curability of the composition to a great extent when it is incorporated into the curing agent of this invention immediately before use. Examples of the cure promoter are preferably tertiary amines such as N,N-dimethylbenzylamine, α-methylbenzyldimethylamine, 2,4,6-tris(dimethylaminomethyl)phenol and hexamethoxymethylmelamine; amine oxides such as N,N-dimethylbenzylamine oxide, phosphorus compounds such as triphenylphosphine; boron amine complexes such as $BF_3$-piperidine and triethanolamine borate; boric acid ester derivative, and aniline-formaldehyde resin. Particularly preferred are tertiary amines such as N,N-dimethylbenzylamine, α-methylbenzyldimethylamine, 2,4,6-tris(dimethylaminomethyl)phenol and phosphorus compounds such as triphenylphosphine. The amount of the cure promoter for use is 0.05 to 5% by weight, preferably 0.1 to 1% by weight, particularly preferably 0.2 to 0.8% by weight, based on the epoxy resin composition. Advantageously, the polyepoxy compound, the epoxy curing agent of this invention and optionally, the above cure promoter are mixed, and a curing reaction is carried out while the resultant mixture is shaped directly or through a so-called B-stage resin in which the mixture partly undergoes the reaction.

The above curing agent may be partially replaced with other curing agent, e.g. polyphenols such as phenol novolak, cresol novolak or polyvinyl phenol, and an anhydrous curing agent such as trimellitic anhydride or phthalic anhydride.

The above epoxy resin composition may further contain a suitable amount of other additive depending upon required functions of a cured product, and examples thereof are inorganic powders such as an alumina powder and wollastonite; a powder of a metal such as aluminum, copper or silver, a dyestuff, a pigment, etc.

The resin mixture before being cured may be formed into a powder or flake form and transfer-molded or compression-molded.

Further, the resin mixture may be used as a coating composition or an adhesive by coating a substrate surface with it in a form of a solution such as a varnish, and drying and curing the resultant coating.

Furthermore, such a varnish may be used to form a composite material by impregnating it into a reinforcing material such as a glass fiber, a glass fabric, a carbon fiber, an aramide fiber, etc., to prepare a so-called pre-preg, and press-molding or autoclave-molding the pre-preg.

The epoxy resin cured product according to this invention has low water vapor absorption and excellent electrical properties and heat resistance, and it can therefore be suitably used in fields of advanced technologies such as an electronic and electric field including a semiconductor sealing agent, aerospace industry, and the like.

The epoxy compound of the formula (II), provided by this invention, can be cured with a conventional epoxy curing agent and can be formed into a cured epoxy resin having excellent heat resistance.

Examples of such a curing agent are amines, ananhydride, a polyamide resin, a polysulfide resin, a boron trifluoride amine complex, a novolak resin, a dicyandiamide, etc.

Specific examples of the above curing agent are (a) aliphatic amines such as diethylenetriamine, triethylenetetramine, 1,3-diaminocyclohexane, isophoronediamine and xylylenediamine; and aromatic amines such as m-phenylenediamine, p-phenylenediamine, 4,4'-diaminodiphenylmethane, 4,4'-diaminodiphenylsulfone, 3,3'-diaminodiphenylsulfone, 2,4-toluylenediamine, 4,4'-diaminodiphenyl ether, 3,4'-diaminodiphenyl ether and an aniline-formalin resin; (b) an adduct of the above aliphatic or aromatic amine with a monoepoxy compound (ethylene oxide, phenylglycidyl ether, butylglycidyl ether, or the like), a polyepoxy compound (diglycidyl ether of bisphenol A, diglycidyl ether of resorcin, or the like), acrylonitrile, or the like; (c) anhydrides such as phthalic anhydride, hexahydrophthalic anhydride, Nadic anhydride, methyl Nadic anhydride, pyromellitic anhydride, benzophenonetetracarboxylic anhydride, trimellitic anhydride, glycerin tristrimellitate, and ethylene glycol trimellitate; (d) a polyamide resin of a dimer acid with diethylenetetramine, triethylenetetramine, or the like; (e) a polysulfide resin having a mercaptan group at each end; (f) a complex of an amine such as aniline, N-methylaniline, benzylamine, ethylamine or the like with boron trifluoride; (g) a low molecular weight novolak resin obtained from phenol, cresol and formalin; and (h) dicyandiamide.

The novel epoxy compound of this invention can be cured with a conventional curing agent for epoxy resin as described above. In particular, it exhibits an excellent effect in use requiring heat resistance when it is cured with an aromatic polyamine and/or dicyandiamide.

Of the above curing agents, 4,4'-diaminodiphenylsulfone and dicyandiamide are particularly preferred.

Concerning the above curing agents, the amines, the polyamide resin, the polysulfide resin, the boron trifluoride amine complex, the novolak resin, etc., are used such that the ratio of the amount of active hydrogen of these curing agents/the epoxy equivalent of the epoxy compound is 0.5 to 1.5 by mole, preferably 0.8 to 1.2 by mole. The anhydride is used such that the ratio of its anhydride group amount/the epoxy equivalent of the epoxy compound is 0.5 to 1.0 by mole, preferably 0.6 to 0.9 by mole. The dicyandiamide is used such that the ratio of its active hydrogen amount/the epoxy equivalent of the epoxy compound is 1/20 to $\frac{1}{3}$ by mole, preferably 1/10 to $\frac{1}{4}$ by mole.

The novel epoxy compound of this invention is cured together with the above epoxy curing agent to form a heat-resistant cured resin.

In this case, the above-described conventional polyepoxy compounds such as a glycidyl ether compound, glycidyl ester compound, N-glycidyl compound and a glycidyl ether ester compound may be used in combination with the epoxy compound of this invention, and a small proportion of a cure promoter may be incorporated.

Examples of the cure promoter are tertiary amines such as triethylamine, tributylamine and dimethylbenzylamine; phenols such as phenol, cresol, butylphenol, nonylphenol, chlorophenol, resorcinol and polyvinylphenol; imidazoles such as imidazole, 2-ethyl-4-methylimidazole; and salts such as acetates of these.

The amount of the cure promoter for use is preferably 0.05 to 5% by weight, more preferably 0.1 to 1% by weight, particularly preferably 0.2 to 0.8% by weight, based on the thermosetting resin comprising the epoxy compound.

The epoxy compound of this invention can be directly cured by adding the curing agent, etc., thereto, as described above. Alternatively, the epoxy compound may dissolved in a solvent, and a curing agent and, optionally, a cure promoter are homogeneously dispersed or dissolved in the mixture, followed by removing the solvent to obtain a homogeneous mixture and curing it. Examples of such a solvent are ketones such as acetone, methyl ethyl ketone, methyl butyl ketone and diethyl ketone; alcohols such as methyl cellosolve and ethyl cellosolve; cyclic ethers such as dioxane and tetrahydrofuran; amides such as dimethylformamide, dimethylacetamide and N-methylpyrrolidone; and aromatic hydrocarbons such as benzene, toluene, xylene and and cumene.

The above thermosetting resin can be formed into a cured product by subjecting it to a curing reacation at a time of molding directly or through a so-called B-stage resin in which part of the resin has reacted.

The curing reaction of the epoxy compound of this invention can proceed at a temperature of 40° C. or higher, and it is carried out under heat preferably at a temperature between 70° C. and 250° C.

The cure time is usually 0.5 to 5 hours. The cured product has further improved heat resistance when it is post-cured preferably at a temperature of 150° C. or higher.

According to this invention, there is provided a cured product of a thermosetting resin comprising the epoxy compound of the formula (II) provided by this invention, and there is further provided a cured product of a thermosetting resin mainly comprising the epoxy compound of the formula (II) provided by this invention.

Further, according to this invention, there is provided a composite material comprising a matrix resin of a cured product of a thermosetting resin comprising the epoxy compound of the formula (II) provided by this invention and a reinforcing material such as a carbon fiber, an aramide fiber or a glass fiber, as described above.

The above cured molded article and composite material of this invention are excellent in water resistance, heat resistance, chemical resistance, mechanical properties, dimensional stability and electrical properties, and are suitably usable in advanced technology fields such as an electronic and electric field including a semiconductor sealing agent, an aerospace industry field, etc.

Further, according to another aspect of this invention, there are provided:

a hydroxycarboxylic acid or its ester, which corresponds to a compound formed by substituting at least part of the following formula

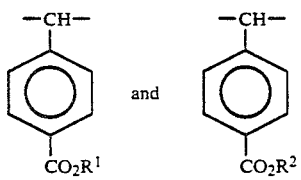

in the formula (I) with a certain special group, and an epoxy compound which corresponds to a compound formed by substituting at least part of the following formula

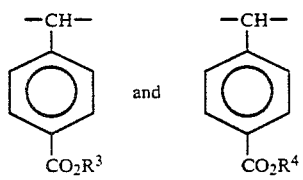

in the formula (II) with a certain special group.

Such a hydroxycarboxylic acid or an ester thereof and such an epoxy compound are usable completely in the same way as the hydroxycarboxylic acid or its ester of the formula (I) and the epoxy compound of the formula (II).

Such a hydroxycarboxylic acid or an ester thereof has the following formula (I)′:

$$\begin{matrix}(OH) & (OH)_m & (OH)_n \\ | & | & | \\ Ar^1-X^1-(Ar^2-X^2)_q-Ar^3\end{matrix} \quad (I)'$$

wherein $Ar^1$, $Ar^2$, $Ar^3$, l, m, n and q are as defined in the formula (I), and $X^1$ and $X^2$ may be same or different and are independently a group selected from the class consisting of

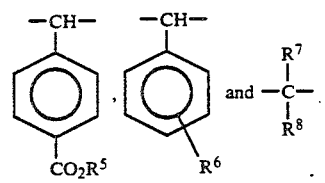

in which $R^5$ is a hydrogen atom or an alkyl group having 1 to 10 carbon atoms, $R^6$ is —OH or —NH$_2$, and $R^7$ and $R^8$ may be same or different and each independently represents a hydrogen atom or an alkyl group having 1 to 10 carbon atoms, provided that at least 15 mol %, preferably at least 20 mol %, particularly preferably at least 25 mol % of each of the $X^1$ and $X^2$ is the group of the following formula

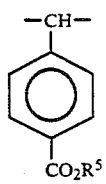

The hydroxycarboxylic acid or its ester of the formula (I)′ can be produced according to the process for the production of the compound of the formula (I) except that part of the aldehyde of the formula (III) is replaced with a compound of the formula (III)′ and/or a compound of the formula (III)″, for example, p-hydroxybenzaldehyde [compound of the formula (III)′] and/or formaldehyde or acetaldehyde [compound of the formula (III)″]

The epoxy compound corresponding to the formula (I)′ has the following formula (II)′.

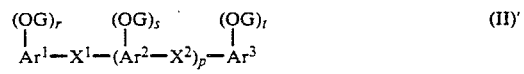

wherein $Ar^1$, $Ar^2$, $Ar^3$, G, r, s, t and p are as defined in the formula (II), and $X^1$ and $X^2$ are as defined in the formula (I)′.

The epoxy compound of the formula (II)′ can be produced according to the process for the production of the epoxy compound of the formula (II) except that the hydroxycarboxylic acid or its ester of the formula (I) is replaced with the compound of the formula (I)′.

It is believed that specific examples of the compounds of the formulae (I)′ and (II)′ are self-evident on the basis of the specific examples of the compounds of the formula (I) and (II) and the definitions of $X^1$ and $X^2$.

As specified hereinabove, there are provided a cured product and a composite material which have excellent water resistance, heat resistance, mechanical properties, dimensional stability and electrical properties, and there are also provided a novel epoxy compound and a precursor thereof which give such a cured product and such a composite material. Further, according to this invention, these epoxy compound and precursor can be produced efficiently and economically. Therefore, this invention produces industrially and practically various effects in addition to these advantages.

This invention will be explained hereinbelow by reference to Examples, which, however, shall not limit this invention.

In Examples, "part" stands for "part by weight" unless otherwise specified.

Infrared absorption spectrum analysis (IR) and nuclear magnetic resonance spectrum analysis (NMR)

used for identifying epoxy compounds obtained in Examples are as follows.

a) Infrared absorption spectrum analysis (IR)

A neat epoxy compound was casted on a KBr plate and measured for infrared absorption spectrum according to a conventional method.

b) Neuclear magnetic resonance spectrum analysis (NMR):

The measurement was made by using d-chloroform as a solvent and tetramethylsilane as a reference.

EXAMPLE 1

(1) 235 Parts of phenol, 25 parts of p-formylbenzoic acid, 0.05 part of p-toluenesulfonic acid onohydrate and 0.07 part of concentrated hydrochloric acid were allowed to react under nitrogen atmosphere at 60° C. for 3 hours with stirring, and then allowed to react for 12 hours with gradually elevating the temperature of the reaction mixture so that the reaction temperature finally reached 160° C. During the reaction, water formed as a result of the reaction was distilled out of the reaction system. The resultant reaction product was taken out of the reactor, 300 parts of toluene was added, and the resultant mixture was washed with 100 parts of water three times. Then, unreacted phenol was distilled off at 80° C. under reduced pressure of 5 mmHg, and further removed by flushing the mixture with steam to give 30 parts of a hydroxycarboxylic acid.

The hydroxycarboxylic acid had a melting point of 130° to 145° C. and a molecular weight, measured by a cryoscopic method using dioxane, of 325. Elemental analysis thereof showed C(%): 75.35, H(%): 5.14.

IR spectrum of the above hydroxycarboxylic acid was shown in FIG. 1, in which a broad peak assigned to hydroxyl groups and carboxyl groups is observed at 3,000 to 3,600 cm$^{-1}$ and a peak assigned to carboxyl groups is observed at 1,690 cm$^{-1}$.

These data shows that the above hydroxycarboxylic acid had the following chemical structure.

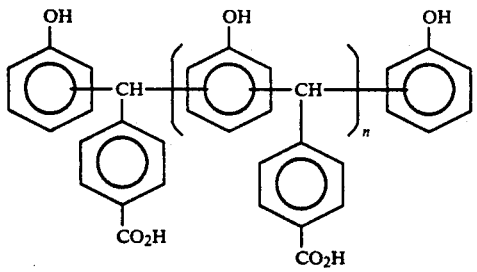

(wherein n≈0)

(2) 11 Parts of the above hydroxycarboxylic acid was added to 46 parts of epichlorohydrin and dissolved therein by heating the mixture to 80° C. 0.7 Part of a 60% aqueous solution of tetraethylammonium chloride was added dropwise over 2 hours, the resultant mixture was held at said temperature for 1 hour, and then 8 g of a 50% aqueous solution of sodium hydroxide was added dropwise over 1 hour. And, the reaction was further continued for 3 hours. After the reaction, epichlorohydrin was recovered by distillation under reduced pressure, and 130 parts of toluene was added to the remainder. The resultant mixture was washed with 50 parts of water, with 50 parts of an aqueous solution of dilute phosphoric acid and further with 50 parts of water five time each to remove an excess amount of sodium hydroxide and precipitated sodium chloride. Toluene was distilled off from the toluene phase to give 14 parts of an epoxy compound having an epoxy equivalent of 208 g/eq and a melting point of not higher than 25° C., which had the following chemical structure. The epoxy compound had a molecular weight, measured by a cryoscopic method using dioxane, of 508.

Figure 2:
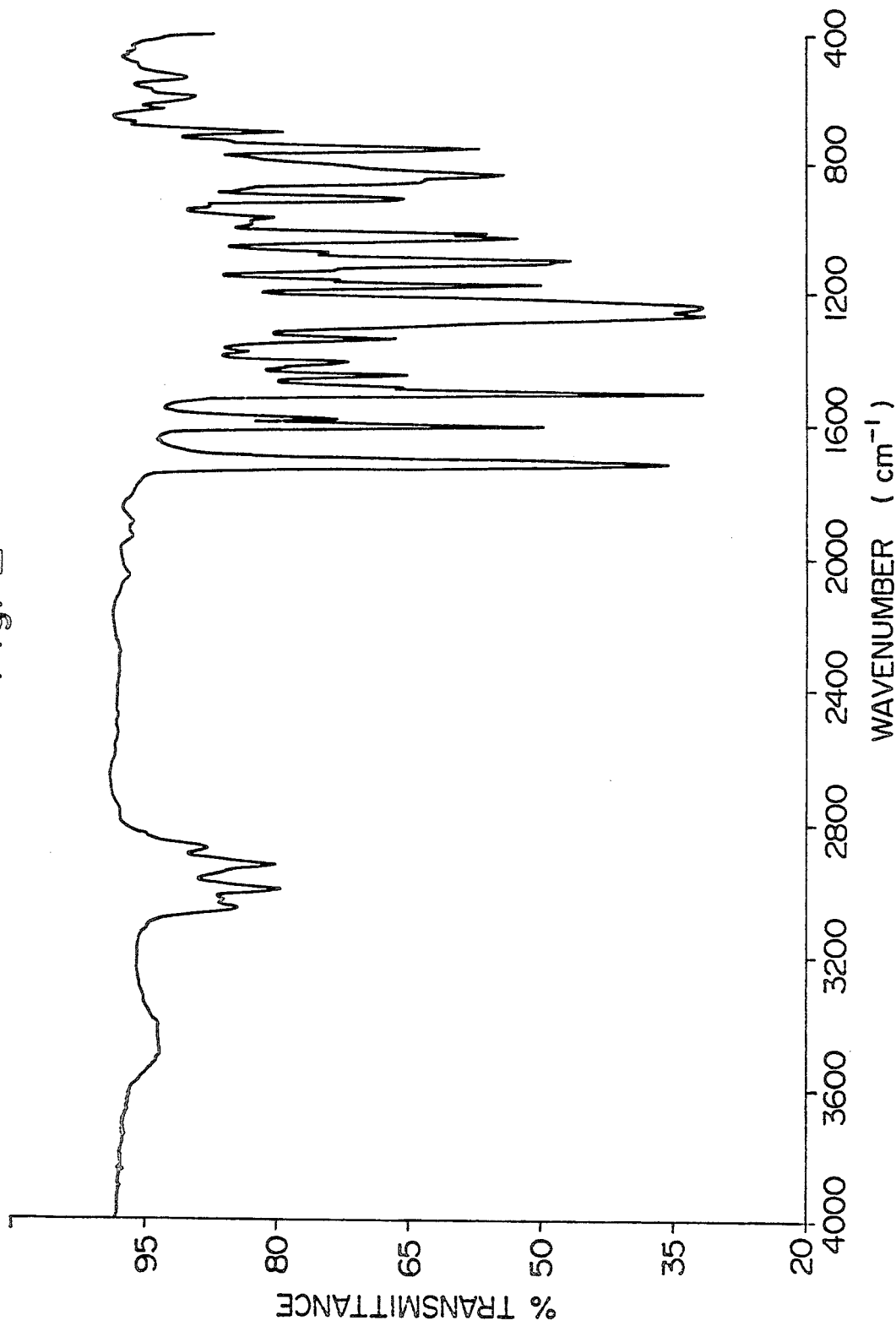
FIG. 2 shows an infrared absorption spectrum of an epoxy compound obtained in Example 1. (2).
Figure 3:
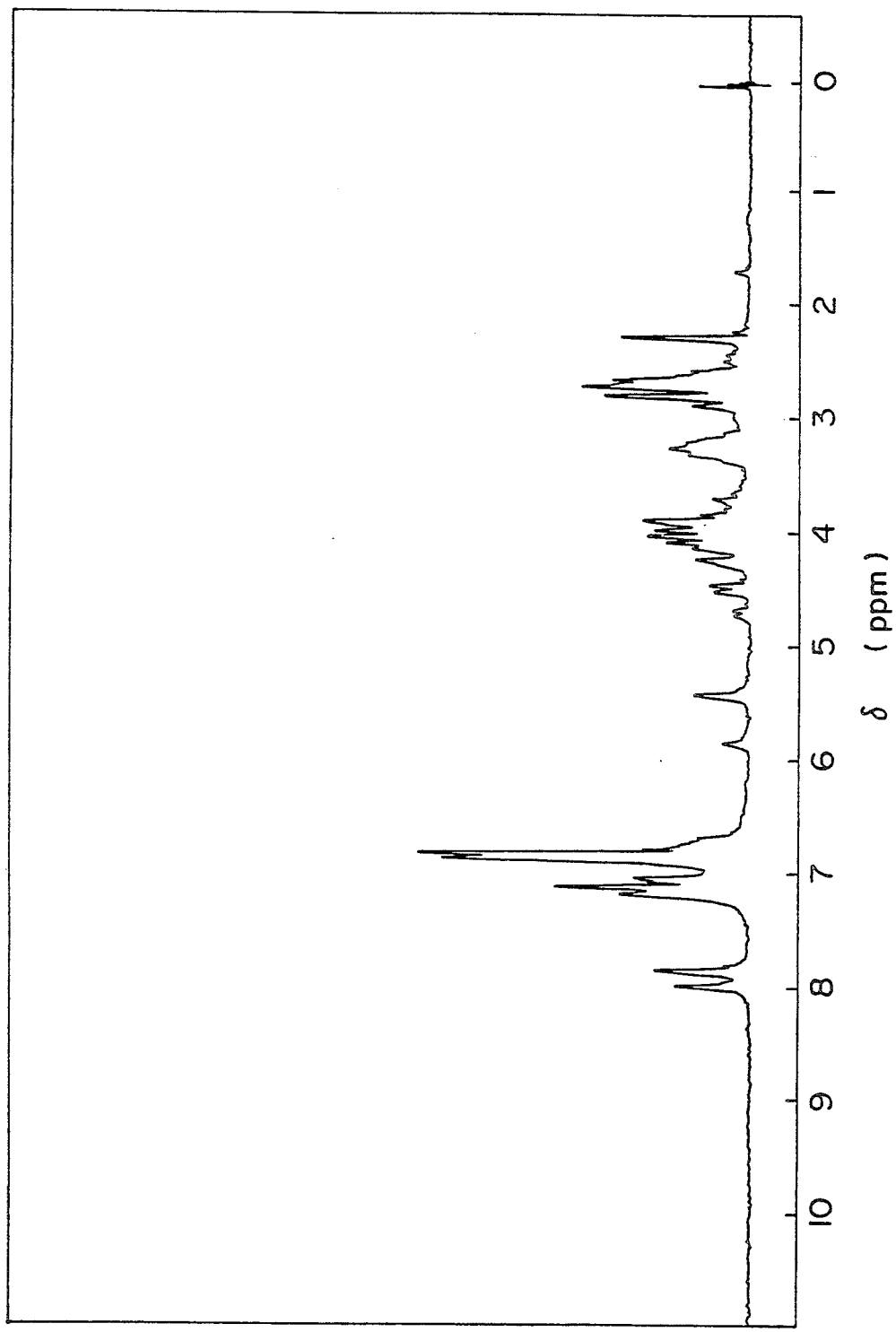
FIG. 3 shows an NMR spectrum of an epoxy compound obtained in Example 1. (2).

IR and NMR spectra of this epoxy compound are shown in FIGS. 2 and 3. In FIG. 2, a peak assigned to carboxyl groups is observed at 1,720 cm$^{-1}$, and a peak assigned to epoxy groups is observed at 910 cm$^{-1}$. In FIG. 3, peaks are observed at 2.2 to 4.8 ppm (m, 5H's of glycidyl group), at 5.2 to 6.2 ppm (m, H of methyne group) and at 6.5 to 8.2 ppm (m, H of aromatic ring).

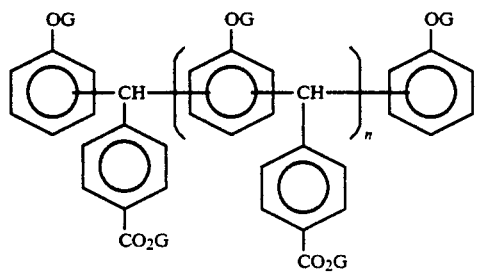

(wherein n≈0, and

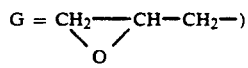

EXAMPLE 2

(1) 1,410 Parts of phenol, 164 parts of methyl p-formylbenzoate, 1.5 parts of p-toluenesulfonic acid monohydrate and 0.4 part of concentrated hydrochloric acid were allowed to react under nitrogen atmosphere at 150° C. for 1 hour with stirring, and then allowed to react for 8 hours with gradually elevating the temperature of the reaction mixture so that the reaction temperature finally reached 161° C. During the reaction, water formed as a result of the reaction was distilled out of the reaction system. The resultant reaction product was taken out of the reactor, 2,000 parts of toluene was added, and the resultant mixture was washed with 600 parts of water three times. Then, toluene was distilled off under reduced pressure, and unreacted phenol was distilled off at 80° C. under reduced pressure of 5 mmHg, and further removed by flushing the mixture with steam to give 311 parts of a hydroxycarboxylic acid derivative.

Figure 4:
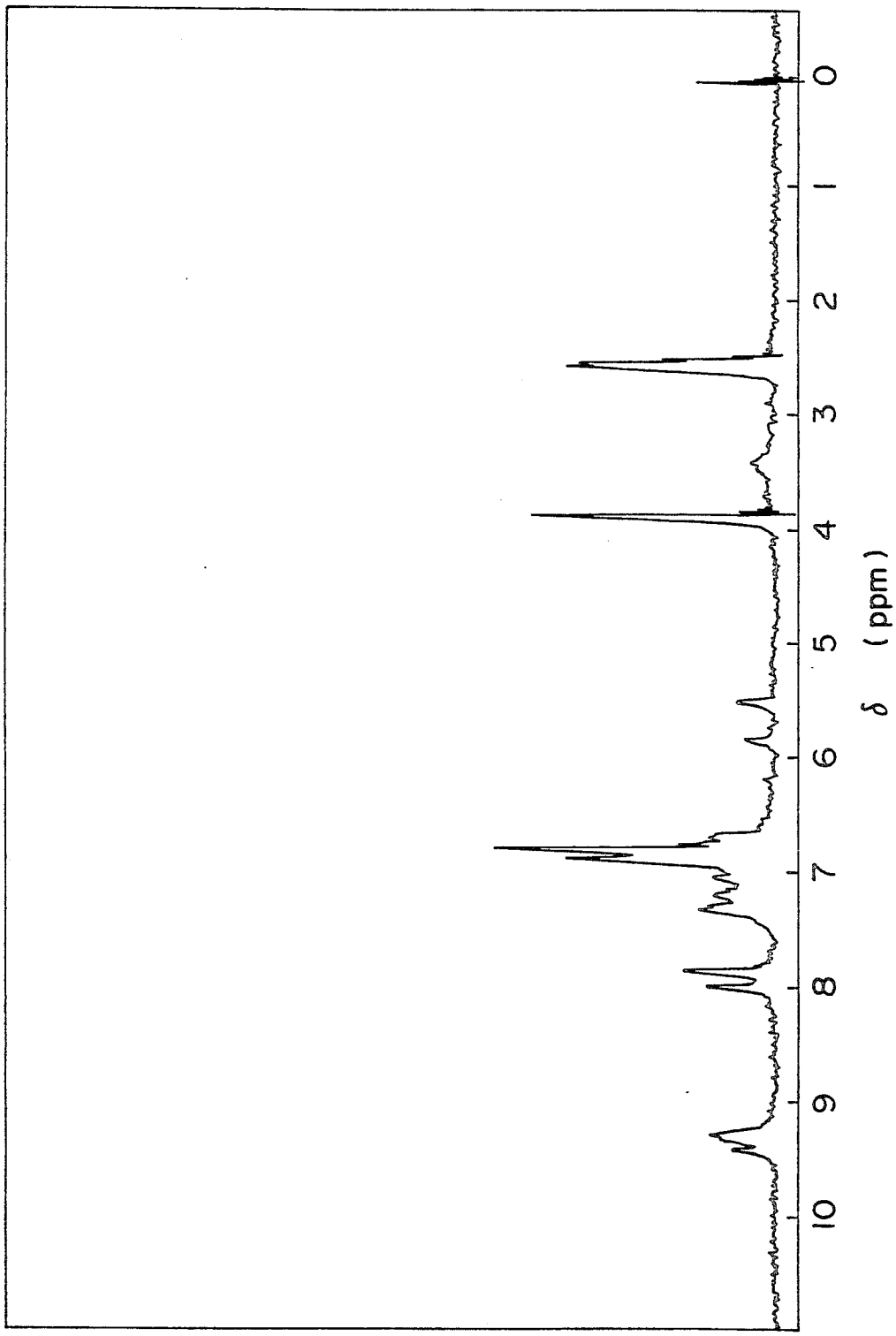
FIG. 4 shows an NMR spectrum of a hydroxycarboxylic acid obtained in Example 2. (1).

NMR spectrum of the resultant product is shown in FIG. 4, in which peaks are observed at 3.8 ppm (s, H of methyl ester), at 5.5 to 6.2 ppm (m, H of methyne), at 6.5 to 8.2 ppm (m, H of aromatic ring) and at 9.2 to 9.5 ppm (m, H of hydroxyl group). This NMR chart shows that 65% of the hydroxycarboxylic acid derivative obtained above was methyl ester.

The hydroxycarboxylic acid derivative had a melting of 115° to 130° C. and a molecular weight, measured by a cryoscopic method using dioxane, of 332. Elemental analysis thereof showed C(%): 75.35, H(%): 5.19.

These data shows that the above hydroxycarboxylic acid derivative had the following chemical structure.

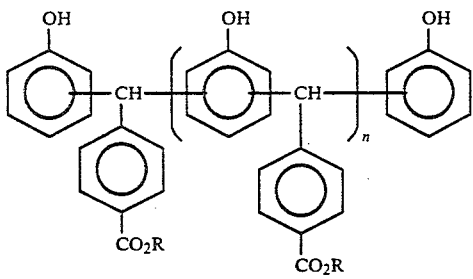

(wherein n≈0, ⅓ of R=H, ⅔ of R=—CH₃)

(2) 214 Parts of the above hydroxycarboxylic acid derivative and 4.4 parts of benzyltrimethylammonium chloride were added to 4,500 parts of epichlorohydrin, and the resultant mixture was allowed to react at 80° C. for 5 hours while it was stirred.

Figure 5:
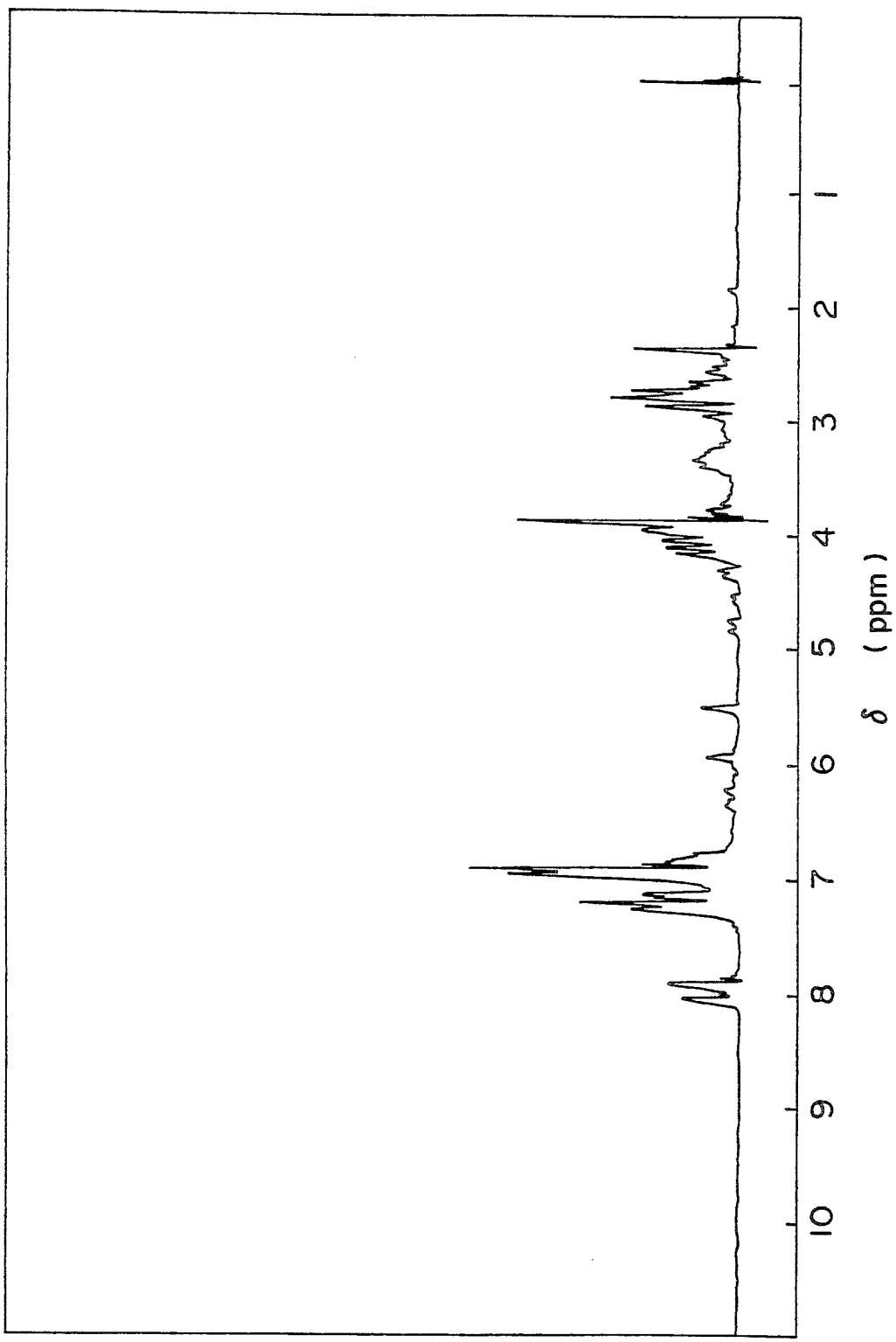
FIG. 5 shows an NMR spectrum of an epoxy compound obtained in Example 2. (2).

After the temperature of the reaction mixture was adjusted to 95° C., 194 parts of a 50% aqueous solution of sodium hydroxide was added dropwise over 1.5 hours at 160 mmHg with stirring. In this case, water formed in the system was distilled out of the system. The resultant reaction mixture was purified in the same way as in Example 1 to give 244 parts of an epoxy compound having an epoxy equivalent of 223 g/eq, a molecular weight, measured by a cryoscopic method using dioxane, of 402 and a melting point of not higher than 25° C., and having the following chemical formula. NMR spectrum of this epoxy compound is shown in FIG. 5, in which a peak is observed at 3.8 ppm (H of methyl ester) in addition to those peaks observed in FIG. 4. NMR showed that 65% of the epoxy compound was methyl ester.

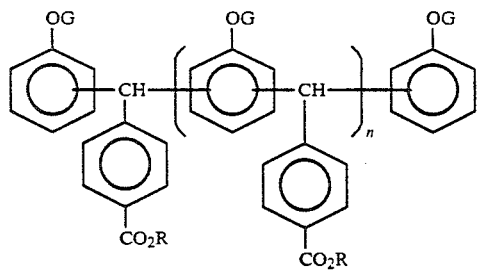

(wherein N≈0,

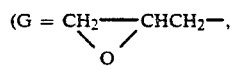

⅓ of R=G, ⅔ of R=—CH₃)

EXAMPLE 3

Figure 6:
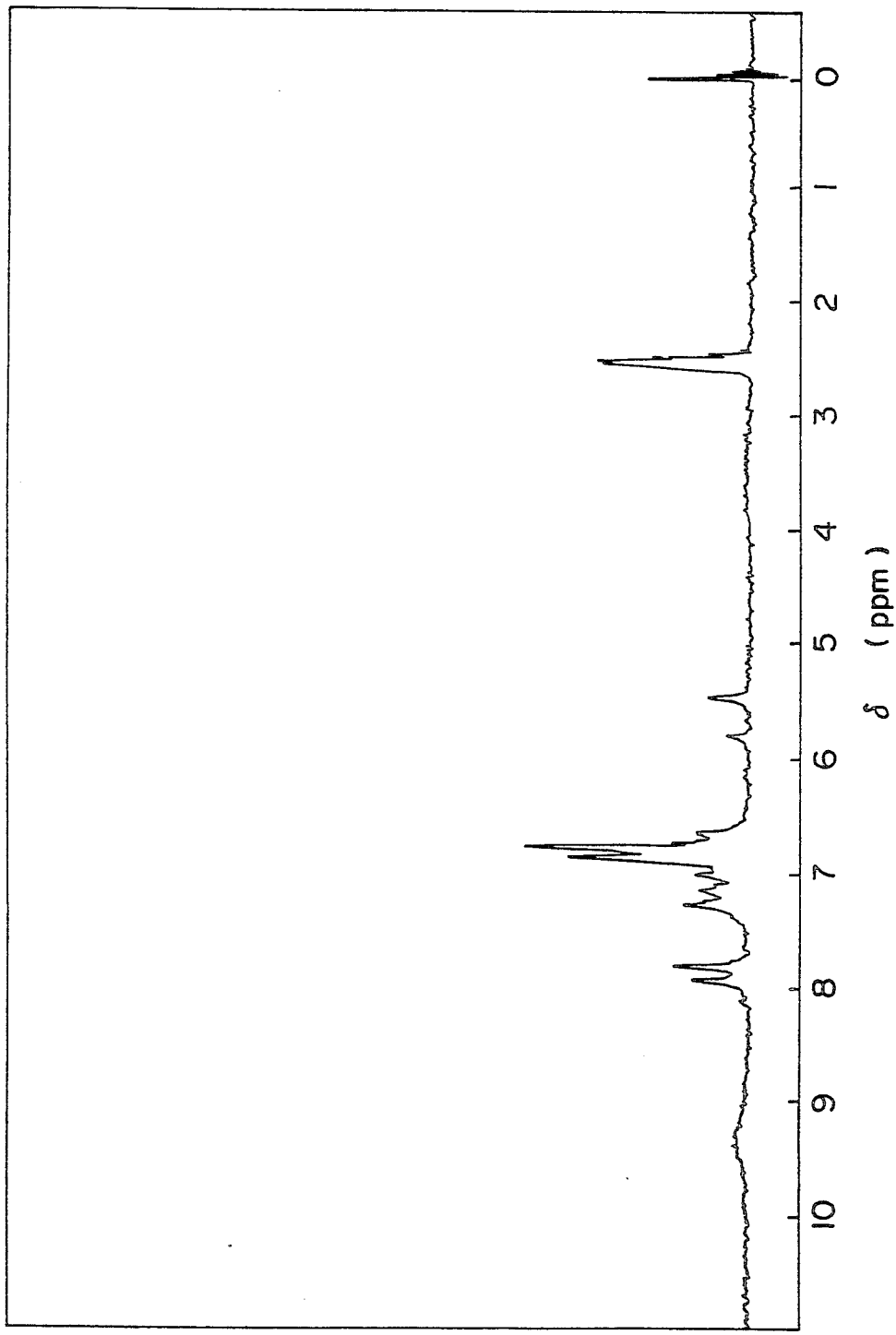
FIG. 6 shows an NMR spectrum of a hydroxycarboxylic acid obtained in Example 3. (1).

(1) 1,500 Parts of a 5% aqueous solution of sodium hydroxide was added to 160 parts of the hydroxycarboxylic acid derivative obtained in Example 2, and the mixture was refluxed under heat for 2 hours to hydrolyze the methyl ester. Then, the hydrolysis product was subjected to acidolysis with a 10% aqueous solution of hydrochloric acid, and the resultant solid was washed with 1,000 parts of water three times and dried at 80° C. under reduced pressure to give 123 parts of a hydroxycarboxylic acid. NMR (FIG. 6) showed that the resultant hydroxycarboxylic acid was completely hydrolyzed. That is, the peak (H of methyl ester) at 3.8 ppm observed in FIG. 4 is not observed in FIG. 6.

The above hydroxycarboxylic acid had a melting point of 133° to 146° C., and a molecular weight, measured by a cryoscopic method using dioxane, of 329. Elemental analysis showed C(%): 75.37, H(%): 5.15.

IR spectrum of this compound is greatly similar to that of the compound obtained in Example 1.(1), and it was found that the compound obtained in this Example had the structural formula shown in Example 1.(1).

(2) The above hydroxycarboxylic acid was subjected to glycidylation in the same way as in Example 2 to give 200 parts of an epoxy compound having an epoxy equivalent of 196 g/eq and a melting point of not higher than 25° C. This epoxy compound had a molecular weight, measured by a cryoscopic method using dioxane, of 502. IR and NMR of this compound were nearly similar to those in FIGS. 2 and 3.

EXAMPLE 4

1,410 Parts of phenol, 164 parts of ethyl p-formylbenzoate, 1.5 parts of p-toluenesulfonic acid monohydrate and 0.4 part of concentrated hydrochloric acid were allowed to react under nitrogen atmosphere at 150° C. for 1 hour with stirring, and then allowed to react for 8 hours with gradually elevating the temperature of the reaction mixture so that the reaction temperature finally reached 161° C. During the reaction, water formed as a result of the reaction was distilled out of the reaction system. Then, unreacted phenol was distilled off from the reaction mixture at 80° C. under reduced pressure of 5 mmHg, and further removed by flushing the mixture with steam. 2,000 Parts of a 10% aqueous solution of sodium hydroxide was added to the resultant compound, and the mixture was refluxed under heat for 2 hours, and then subjected to acidolysis with a 10% aqueous solution of hydrochloric acid. The resultant solid was washed with 1,000 parts of water three times and dried under reduced pressure at 80° C.

The resultant hydroxycarboxylic acid had a melting point of 148° to 195° C. and a molecular weight, measured by a cryoscopic method using dioxane, of 587. Elemental analysis showed C(%): 73.98, H(%): 4.01.

Figure 7:
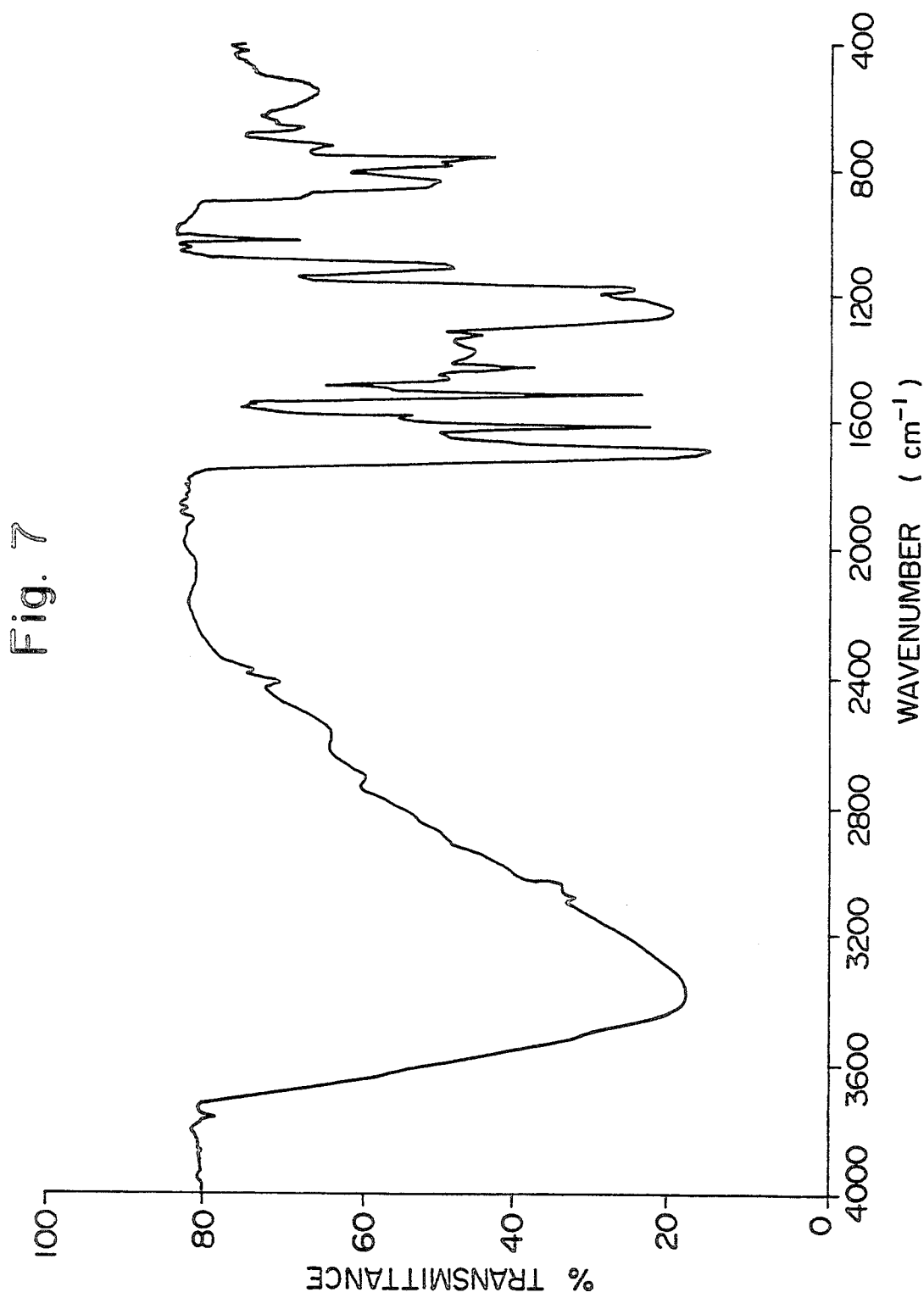
FIG. 7 shows an infrared absorption spectrum of a hydroxycarboxylic acid obtained in Example 4.

IR spectrum of this compound is shown in FIG. 7, in which, similarly to those in FIG. 1, a broad peak assigned to a hydroxyl group and a carboxyl group is observed at 3,000 to 3,600 cm⁻¹ and a peak assigned to carbonyl of a carboxyl group is observed at 1,690 cm⁻¹.

These data showed that the above hydroxycarboxylic acid had the following chemical structure.

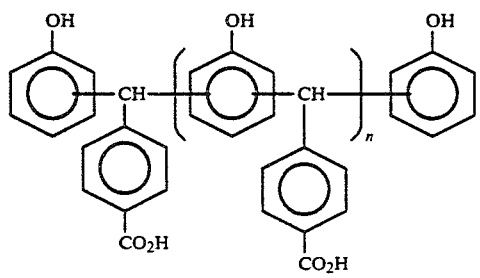

(wherein mean value of n=1.2).

EXAMPLE 5 AND COMPARATIVE EXAMPLES 1 AND 2

20 Parts of the epoxy compound synthesized in Example 1 and 4,4'-diaminodiphenylsulfone were mixed such that the amount of the epoxy group of the epoxy compound and that of the active hydrogen atom of 4,4'-diaminodiphenylsulfone became equimolar, and heated to form a homogeneous solution. Immediately thereafter, the solution was charged into a mold heated to 220° C. to carry out a curing reaction for 1 hour. The resultant molded piece was cured at 220° C. for 4 hours, and then measured for a glass transition temperature by a DMA (model 1090, supplied by du Pont) at a rate of temperature rise of 10° C./minute.

For comparison, a diglycidyl ether of bisphenol A (epoxy equivalent 190 g/eq) and a polyglycidyl ether of phenol novolak (epoxy equivalent 178 g/eq) were cured with 4,4'-diaminodiphenylsulfone in the same way as above (Example 5), and the resultant resins were measured for a glass transition temperature.

Table 1 shows the results.

TABLE 1

|  | Epoxy compound | Glass transition temperature (°C.) |
|---|---|---|
| Example 5 | Synthesized in Example 1 | 304 |
| Comparative Example 1 | Diglycidyl ether of bisphenol A | 238 |
| Comparative Example 2 | Polyglycidyl ether of phenol novolak | 266 |

The results shown in Table 1 show that the cured product of the epoxy compound of this invention has excellent heat resistance over those of conventional compounds.

EXAMPLE 6

19.6 Parts of the epoxy compound synthesized in Example 1 and 2 parts of dicyandiamide were heated to form a homogeneous solution, and immediately thereafter, the solution was charged into a mold heated to 200° C. to carry out a curing reaction for 1 hour.

The resultant molded piece was cured at 220° C. for 5 hours, and measured for a glass transition temperature in the same way as in Example 5.

The resultant cured product had a glass transition temperature of 290° C. and excellent heat resistance.

EXAMPLE 7 AND COMPARATIVE EXAMPLE 3

20 Parts of the epoxy compound obtained in Example 3 was dissolved in 30 parts of acetone, and 4,4'-diaminodiphenylsulfone was added such that the amount of the epoxy group of the epoxy compound and that of the active hydrogen atom of the 4,4'-diaminodiphenylsulfone became equimolar to form a homogeneous solution. And, the homogeneous solution was formed, and acetone was evaporated at 80° C. Then, the solution was subjected to a curing reaction in a press molding machine according to a conventional method under a pressure of 10 kg/cm³ at 200° C. for 1 hour to give a molded piece having a thickness of 3 mm, a width of 6 mm and a length of 120 mm. This molded piece was cured at 220° C. for 4 hours, and then measured for a glass transition temperature by a DMA (model 1090, supplied by du Pont) at a rate of temperature rise of 10° C./minute.

For comparison, 6.2 parts of 4,4'-diaminodiphenylsulfone and 17.5 parts of a diglycidyl ether of bisphenol A (epoxy equivalent 175 g/eq) were added to 30 parts of acetone, and a resin was obtained by the same procedure as above (Example 7). The resulting resin was measured for a glass transition temperature. The results are shown in Table 2.

TABLE 2

|  | Epoxy compound | Glass transition temperature (°C.) |
|---|---|---|
| Example 7 | Synthesized in Example 3 | 309 |
| Comparative Example 3 | Diglycidyl ether of bisphenol A | 242 |

The results in Table 2 show that the cured product of the epoxy compound of this invention has excellent heat resistance over that of a conventional compound.

EXAMPLES 8-11

(1) A phenolic compound of which the name and amount are shown in Table 3 and 0.3 part of p-toluenesulfonic acid monohydrate were dissolved in 90 parts of toluene, and the mixture was heated to form a solution having a temperature of 100° C. And, a solution of 92 parts of methyl p-formylbenzoate in 92 parts of toluene was added dropwise to the above solution over 2 hours under nitrogen atmosphere with stirring.

While water formed during the reaction was distilled out of the system, the reaction was further continued for 1 hour, and the resultant reaction mixture was further allowed to react at 110° C. for 1 hour. 3 Parts of concentrated hydrochloric acid was added, and the resultant mixture was allowed to react for 1 hour, and further allowed to react at 120° C. for 3 hours. 700 Parts of a 10% aqueous solution of sodium hydroxide was added to the resultant reaction mixture, the mixture was hydrolyzed under reflux by heating for 2 hours, a toluene phase was then removed, and a water phase was acidolyzed with a 10% aqueous solution of hydrochloric acid aqueous solution to give a solid. The solid was washed with 300 parts of water three times, and then an unreacted phenolic compound was removed by distillation under reduced pressure and flushing with steam to give a hydroxycarboxylic acid. Table 3 shows yields, melting points, molecular weights measured by a cryoscopic method using dioxane, elemental analysis results and the structures of the resulting hydroxycarboxylic acids identified by IR and NMR.

TABLE 3

|  | Phenolic compound ( ) = amount (part) | Yield (part) | Melting point (°C.) | Molecular weight | Elemental analysis (%) C | Elemental analysis (%) H | Structure |
|---|---|---|---|---|---|---|---|
| Ex. 8 | Resorcinol (182) | 184 | 149–161 | 402 | 68.19 | 4.40 | mean value of q in formula (I) = 0.2 |
| Ex. 9 | Cresol (178) | 165 | 143–159 | 372 | 75.71 | 5.60 | mean value of q in |

TABLE 3-continued

| | Phenolic compound ( ) = amount (part) | Yield (part) | Melting point (°C.) | Molecular weight | Elemental analysis (%) C | H | Structure |
|---|---|---|---|---|---|---|---|
| Ex. 10 | α-naphthol (162) | 167 | 149–162 | 428 | 78.9 | 4.70 | formula (I) = 0.1 mean value of q in formula (I) = 0 |
| Ex. 11 | Bisphenol A (256) | 231 | 153–179 | 580 | 77.50 | 6.05 | mean value of q in formula (I) = 0 |

(2) 100 Parts of the hydroxycarboxylic acid obtained above and 2 parts of benzyltrimethylammonium chloride were added to 2,000 parts of epichlorohydrin, and the resultant mixture was allowed to react under reflux by heating with stirring for 5 hours. The reaction mixture was adjusted to 95° C., and 100 parts of a 50% aqueous solution of sodium hydroxide was added dropwise at 160 mmHg with stirring over 1.5 hours. In this case, water formed in the system was distilled off. The resultant reaction mixture was purified in the same way as in Example 1.(1). Table 4 shows yields, melting points, epoxy equivalents, elemental analysis results and structures of the epoxy compounds identified by IR and NMR.

TABLE 4

| | Yield (part) | Melting point (°C.) | Epoxy equivalent (g/eq) | Elemental analysis (%) C | H | Structure |
|---|---|---|---|---|---|---|
| Ex. 8 | 121 | 35–43 | 148 | 66.50 | 5.60 | mean value of p in formula (II) = 0.2 |
| Ex. 9 | 103 | not higher than 35 | 190 | 71.1 | 6.08 | mean value of p in formula (II) = 0.1 |
| Ex. 10 | 101 | 85–102 | 212 | 75.39 | 5.40 | mean value of p in formula (II) = 0 |
| Ex. 11 | 105 | 91–115 | 198 | 73.19 | 6.37 | mean value of p in formula (II) = 0 |

EXAMPLE 12

100 Parts of the hydroxycarboxylic acid obtained in Example 1.(1) and 3 parts of benzyltriethylammonium chloride were added to 2,200 parts of β-methylepichlorohydrin, and the resultant mixture was allowed to react under reflux by heating with stirring for 5 hours. The reaction mixture was adjusted to 95° C., and 100 parts of a 50% aqueous solution of sodium hydroxide was added dropwise at 160 mmHg with stirring over 1.5 hours. In this case, water formed in the system was distilled off. The resultant reaction mixture was purified in the same way as in Example 1.(2) to yield 121 parts of an epoxy compound. The epoxy compound had a melting point of not higher than 35° C. and an epoxy equivalent of 202 g/eq, and elemental analysis thereof showed C(%); 72.40, H(%); 6.40. Its structure identified by NMR and IR is as follows.

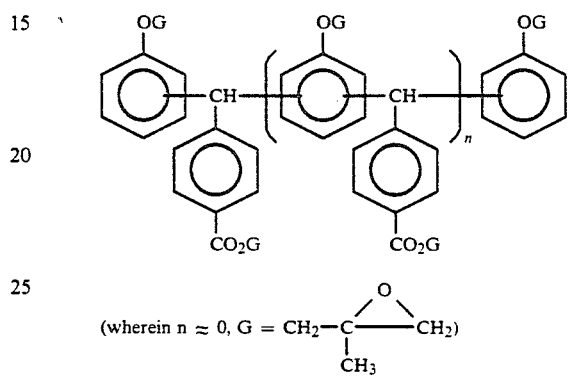

(wherein $n \approx 0$, $G = CH_2-\underset{CH_3}{\overset{}{C}}-CH_2$ with epoxide)

EXAMPLE 13

632 Parts of phenol, 4 parts of hydrochloric acid and 1.2 parts of p-toluenesulfonic acid monohydrate were preliminarily heated in an oil bath at 100° C. Then, a homogeneous solution of 368 parts of methyl p-formylbenzoate in 368 parts of toluene at 40° C. was added dropwise over 2 hours under nitrogen atmosphere with stirring. The resultant mixture was allowed to react for 1 hour, and the bath temperature was elevated to 110° C. to continue the reaction further for 1 hour. Thereafter, 12 parts of concentrated hydrochloric acid was added and the reaction was further continued for 1 hour. The bath temperature was elevated to 140° C. and the reaction was further continued for 1.5 hours. In this case, water formed as a result of the reaction was distilled out of the system. 5 Parts of a 50% aqueous solution of sodium hydroxide was added to the resultant reaction mixture, and the mixture was stirred for 15 minutes. Then, toluene and unreacted phenol were distilled off under reduced pressure. 3,000 Parts of a 10% aqueous solution of sodium hydroxide was added to the reaction mixture, and the mixture was allowed to react for 5 hours under reflux by heating.

The resultant hydrolysis product was cooled to 70° C., 4,500 parts of epichlorohydrin was added, and the resultant mixture was allowed to react for 5 hours with stirring under nitrogen atmosphere. Epichlorohydrin was separated with a separating funnel, and the remainder was washed with 1,000 parts of water, with 1,000 parts of an aqueous solution of dilute phosphoric acid, and further with water five times to remove an excess amount of the sodium hydroxide and precipitated sodium chloride. Then, epichlorohydrin was distilled off under reduced pressure, and phenylglycidyl ether partly formed as a by-product was distilled off under reduced pressure at 150° C. to give 821 parts of an epoxy compound of the following formula, which had an epoxy equivalent of 210 g/eq and a melting point of not higher than 40° C. This epoxy compound had a molecular weight, measured by a cryoscopic method using dioxane, of 524.

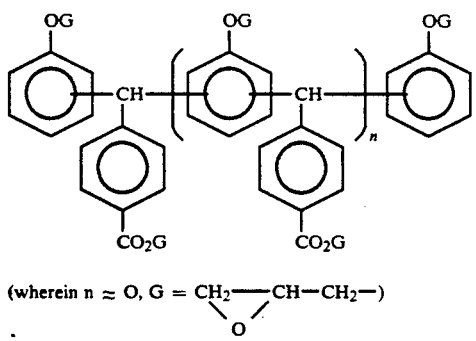

(wherein n ≥ 0, G = CH$_2$—CH—CH$_2$—)
$\phantom{(wherein n ≥ 0, G = CH_2}$\O/

EXAMPLE 14

4,4'-Diaminodiphenylsulfone was added to 30 parts of the epoxy compound obtained in Example 1.(2) such that the amount of the epoxy group and the amount of active hydrogen atom of the 4,4'-diaminodiphenylsulfone became equimolar. The resultant mixture was heated to 150° C. to form a homogeneous solution. 0.23 Part of a trifluoroboran-monoethylamine complex was added to and homogeneously dissolved in the solution, and the resultant solution was allowed to undergo a curing reaction at 180° C. for 5 hours.

The resultant molded plate was measured for a heat distortion temperature with a HDT and VSP tester supplied by Toyo Seiki Seisakusho (this measurement method was also used in Examples hereinafter) to show 281° C. It was thus found to have excellent heat resistance.

EXAMPLE 15

4,4'-Diaminodiphenylmethane was added to 100 parts of the epoxy compound obtained in Example 1.(2) such that the amount of the epoxy group and the amount of active hydrogen atom of the 4,4'-diaminodiphenylmethane became equimolar. The resultant mixture was heated to 150° C. to form a homogeneous solution, and allowed to undergo a curing reaction in a mold preliminarily heated to 180° C. for 1 hour. The resultant molded plate was cured at 200° C. for 2 hours and at 220° C. for 2 hours, and then, the cured plate was measured for a heat distortion temperature to show 256° C. It was thus found to have excellent heat resistance.

EXAMPLE 16

(1) 86.1 Parts of the epoxy compound obtained in Example 1.(2) and 63.9 parts of methyl Nadic anhydride (liquid) were heated to 100° C. to form a homogeneous solution. 1.5 Parts of benzyldimethylamine was added to and homogeneously mixed with this solution, and the resultant mixture was subjected to a curing reaction for 1 hour in a mold preliminarily heated to 150° C. The resultant molded plate was cured at 175° C. for 2 hours, at 220° C. for 2 hours and further at 250° C. for 6 hours.

The resultant molded plate was measured for a heat distortion temperature to show 270° C., and it was thus found to have excellent heat resistance.

(2) 100 Parts of the epoxy compound obtained in Example 1.(2) and 50 parts of phenol novolak having a molecular weight of 350 were mutually dissolved at 120° C. to form a homogeneous solution. And, 2 parts of triphenylphosphine was added to and dissolved in the solution. The resultant mixture was subjected to a curing reaction in a mold preliminarily heated to 180° C. for 1 hour. The resultant molded plate was cured at 200° C. for 5 hours. The resultant molded plate was measured for a heat distortion temperature to show 204° C., and it was thus found to have excellent heat resistance.

EXAMPLE 17

80 Parts of the epoxy compound obtained in Example 1.(2), 20 parts of diglycidyl ether of bisphenol A having an epoxy equivalent of 178 g/eq and 4,4'-diaminodiphenylsulfone were mutually dissolved such that the amount of the epoxy group and the amount of active hydrogen atom of the 4,4'-diaminodiphenylsulfone became equimolar. The resultant mixture was heated to 150° C. to form a homogeneous solution, and allowed to undergo a curing reaction in a mold preliminarily heated to 200° C. for 1 hour. The resultant molded plate was cured at 220° C. for 5 hours and at 230° C. for 2 hours, and the cured plate was measured for a heat distortion temperature to show 269° C. It was thus found to have excellent heat resistance.

EXAMPLE 18

80 Parts of the epoxy compound obtained in Example 1.(2), 20 parts of a phenol novolak type epoxy having an epoxy equivalent of 178 g/eq and 4,4'-diaminodiphenylsulfone were mutually dissolved such that the amount of the epoxy group and the amount of active hydrogen atom of the 4,4'-diaminodiphenylsulfone became equimolar. The resultant mixture was heated to 150° C. to form a homogeneous solution, and allowed to undergo a curing reaction in a mold preliminarily heated to 200° C. for 1 hour. The resultant molded plate was cured at 220° C. for 5 hours and at 230° C. for 2 hours, and the cured plate was measured for a heat distortion temperature to show 275° C. It was thus found to have excellent heat resistance.

EXAMPLE 19 AND COMPARATIVE EXAMPLE 4

30 Parts of the epoxy compound obtained in Example 1.(2) and 4,4'-diaminodiphenylsulfone were mutually dissolved such that the amount of the epoxy group and the amount of active hydrogen atom of the 4,4'-diaminodiphenylsulfone became equimolar. The resultant mixture was heated to 150° C. to form a homogeneous solution, and allowed to undergo a curing reaction in a mold preliminarily heated to 200° C. for 1 hour. The resultant molded plate was cured at 220° C. for 5 hours and at 230° C. for 2 hours.

The cured plate was measured for flexural properties according to ASTM D790. Table 5 shows the results.

For comparison, the above procedure was repeated except that tetraglycidylmethylenedianiline was used in place of the epoxy compound, and the Table 5 also show the results.

Table 5 shows that the cured product of this invention has excellent flexural properties at a high temperature over a conventional cured product.

TABLE 5

| | Epoxy compound | Measurement temperature (°C.) | Flexural properties (kg/mm$^2$) | |
|---|---|---|---|---|
| | | | Strength | Modulus |
| Ex. 19 | Epoxy | 230 | 7.8 | 246 |

TABLE 5-continued

| | Epoxy compound | Measurement temperature (°C.) | Flexural properties (kg/mm²) | |
|---|---|---|---|---|
| | | | Strength | Modulus |
| | compound of | 250 | 6.7 | 225 |
| | Example 1. (2) | 270 | 4.8 | 187 |
| C Ex. 4 | Tetraglycidyl- | 230 | 5.9 | 174 |
| | methylene- | 250 | 3.1 | 119 |
| | dianiline | 270 | 0.4 | 13 |

EXAMPLE 20 AND COMPARATIVE EXAMPLE 5

30 Parts of the epoxy compound obtained in Example 1. (2) and 4,4'-diaminodiphenylsulfone were mutually dissolved such that the amount of the epoxy group and the amount of active hydrogen atom of the 4,4'-diaminodiphenylsulfone became equimolar. The resultant mixture was heated to 150° C. to form a homogeneous solution, and allowed to undergo a curing reaction in a mold preliminarily heated to 200° C. for 1 hour. The resultant molded plate was cured at 220° C. for 5 hours and at 230° C. for 2 hours.

The resultant molded plate was cut into test piece having a size of 10 mm×50 mm×3 mm, and the test piece was immersed in boiling water for 10 days so that the water absorption determined by the following equation was reached saturation, i.e. 5.4%.

$$\text{Water absorption (\%)} = \frac{[\text{wet sample weight (g)} - \text{dry sample weight (g)}]}{\text{dry sample weight (g)}} \times 100$$

For comparison, the above procedure was repeated except that tetraglycidylmethylenedianiline or a glycidyl ether glycidyl esterification product of p-hydroxybenzoic acid was used in place of the above epoxy compound. The resultant test piece formed from the tetraglycidylmethylenedianiline had a water absorption of 6.6%, and the resultant test piece formed from the glycidyl ether glycidyl esterification product of p-hydroxybenzoic acid caused swelling during the treatment in boiling water.

These results show that the a molded article formed from the epoxy compound of this invention had better water absorption although the epoxy compound of this invention contains a glycidyl ester bond.

EXAMPLE 21 AND COMPARATIVE EXAMPLE 6

900 Parts of the epoxy compound obtained in Example 1. (2) and 4,4'-diaminodiphenylsulfone were homogeneously dissolved in 750 parts of acetone such that the amount of the epoxy group and the amount of active hydrogen atom of the 4,4'-diaminodiphenylsulfone became equimolar, whereby a resin solution for immersion was prepared.

A carbon fiber (3,000 filaments (1;800 De), Torayca T 400, supplied by Toray Industries Inc.) was immersed in the above resin solution for impregnation, and taken up around a drum having a width of 31.5 cm such that 323 filaments of the fiber were unidirectionally and uniformly wound on the drum widthwise. Then, the wound drum was heat-treated in a dryer at 65° C. for 45 minutes while acetone was removed. After the heat treatment, the winding filaments were cut in one place to give plate-like prepregs having a width of 31.5 cm.

17 Sheets of the prepregs obtained above were laminated such that the filaments' directions were uniform, and the laminate was allowed to undergo a curing reaction with a press-molding machine under pressure of 60 kg/cm² at 180° C. for 40 minutes to give a molded article having a thickness of 3 mm, a width of 315 mm and a length of 315 mm. This molded article was cured at 220° C. for 5 hours and 230° C. for 2 hours, and the cured article was measured for flexural properties according to ASTM D-970. Table 6 shows the results.

For comparison, the above procedure and measurement were repeated except that tetraglycidylmethylenedianiline was used in place of the epoxy compound. Table 6 also shows the results.

Table 6 shows that the molded article formed from the epoxy compound of this invention has excellent flexural properties at a high temperature over that formed from a conventional compound.

TABLE 6

| | Epoxy compound | Measurement temperature (°C.) | Flexural properties (kg/mm²) | |
|---|---|---|---|---|
| | | | Strength | Modulus |
| Ex. 21 | Epoxy | 230 | 83 | 11,000 |
| | compound of | 250 | 71 | 10,600 |
| | Example 1. (2) | 270 | 58 | 10,100 |
| C Ex. 6 | Tetraglycidyl- | 230 | 61 | 9,400 |
| | methylene- | 250 | 32 | 5,300 |
| | dianiline | 270 | 18 | 3,600 |

EXAMPLE 22 AND COMPARATIVE EXAMPLE 7

The molded plates prepared in Examples 21 and Comparative Example 6 were immersed in boiling water for 10 days, and the plates were measured for flexural properties. Table 7 shows the results. The results of Table 7 show that the molded plate formed from the epoxy compound of this invention has excellent flexural properties under humidity and heat over that formed from a conventional compound.

TABLE 7

| | Epoxy compound | Measurement temperature (°C.) | Flexural properties (kg/mm²) | |
|---|---|---|---|---|
| | | | Strength | Modulus |
| Ex. 22 | Epoxy | 150 | 93 | 12,800 |
| | compound of | 200 | 69 | 12,000 |
| | Example 1. (2) | 230 | 51 | 10,500 |
| C Ex. 7 | Tetraglycidyl- | 150 | 80 | 11,300 |
| | methylene- | 200 | 33 | 6,000 |
| | dianiline | 230 | 24 | 5,200 |

EXAMPLE 23

1.5 Parts of p-toluenesulfonic acid monohydrate was dissolved in 603 parts of phenol, and the resultant mixture was heated to 100° C. to form a solution. A solution of 164 parts of p-formylbenzoic acid in 164 parts of toluene was added dropwise to the above solution over 2 hours under nitrogen atmosphere with stirring. While water formed during the reaction was distilled out of the system, the mixture was further allowed to react for 1 hour, and the reaction mixture was further allowed to react at 110° C. for 2 hours and at 120° C. for 3 hours.

1,250 Parts of a 10% aqueous solution of sodium hydroxide was added to the resultant reaction mixture, and the resultant mixture was subjected to hydrolysis under reflux by heating. Then, a toluene phase was separated off, and a water phase was acidolyzed with a 10% aqueous solution of hydrochloric acid. The resultant solid was dissolved in 1,500 parts of methyl isobutyl ketone, washed with 600 parts of water three times, and then methyl isobutyl ketone and phenol were distilled off under reduced pressure to give 295 parts of a polyhydroxycarboxylic acid.

The above polyhydroxycarboxylic acid had a melting point of 130° to 145° C. and a molecular weight, measured by a cryoscopic method using dioxane, of 415. Elemental analysis thereof showed C(%); 74.87, H(%); 4.92.

IR and NMR analysis of the above hydroxycarboxylic acid showed that it had the following chemical structure.

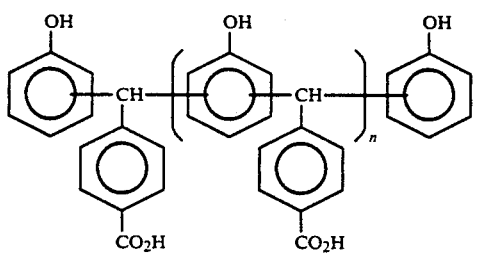

(wherein n≈0.4)

EXAMPLES 24 AND 25 AND COMPARATIVE EXAMPLE 8

100 Parts of an epoxy resin (a phenol novolak type epoxy having an epoxy equivalent of 179 g/eq) and 50 parts of the polyhydroxycarboxylic acid prepared in Example 1. (1) or 23 as a curing agent were charged into a test tube, and homogeneously mixed with each other at 120° C. Then, 2 parts of triphenylphosphine as a cure promoter was added, and homogeneously mixed with the mixture in the test tube. The resultant mixture was charged into a mold preliminarily heated to 180° C. to allow the mixture to react for 1 hour. The cured product was taken out, and subjected to post-cure treatment at 180° C. for 5 hours.

Table 8 shows heat distortion temperatures (HDT) of cured products obtained above.

For comparison, the procedure of Examples 24 and 25 was repeated except that phenol formalin novolak having a molecular weight of 504 was used in place of the polyhydroxycarboxylic acid, and the resultant cured product was measured for a heat distortion temperature. Table 8 also shows the result.

TABLE 8

| Curing agent | | HDT (°C.) |
|---|---|---|
| Example 24 | Polyhydroxycarboxylic acid prepared in Example 1. (1) | 145 |
| Example 25 | Polyhydroxycarboxylic acid prepared in Example 23 | 151 |
| Comparative Example 8 | Phenol formalin novolak | 132 |

EXAMPLES 26 AND 27 AND COMPARATIVE EXAMPLE 9

2 Parts of an epoxy resin (a phenol novolak type epoxy having an epoxy equivalent of 179 g/eq) and 1.2 parts of the polyhydroxycarboxylic acid prepared in Example 1. (1) or 23 as a curing agent were charged into a test tube, and homogeneously mixed with each other at 120° C. Then, 0.04 part of triphenylphosphine as a cure promoter was added and homogeneously mixed with the mixture in the test tube. The test tube was immersed in an oil bath at 180° C. to measure the temperature of the resin solution in the test tube.

Table 9 shows times required for reaching a maximum exothermic temperature from the bath temperature (180° C.) (maximum exothermic temperature attainable time).

For comparison, the above procedure and measurement were repeated except that the same phenol formalin novolak as that used in Comparative Example 8 was used in place of the above polyhydroxycarboxylic acid prepared in Example 26 or 27. Table 9 also shows the result.

It was found that the use of the polyhydroxycarboxylic acid of this invention makes the reaction faster.

TABLE 9

| | Curing agent | Maximum exothermic temperature attainable time (sec.) |
|---|---|---|
| Example 26 | Polyhydroxycarboxylic acid prepared in Example 1. (1) | 14 |
| Example 27 | Polyhydroxycarboxylic acid prepared in Example 23 | 11 |
| Comparative Example 9 | Phenol formalin novolak | 25 |

What is claimed is:

1. A compound selected from a hydroxycarboxylic acid or its ester of the formula (I)

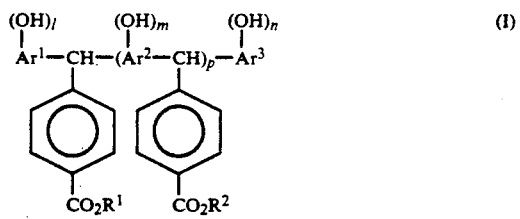

wherein:

Ar$^1$, Ar$^2$ and Ar$^3$ may be same or different and each independently represents a benzene skeleton, a naphthalene skeleton or a skeleton of the formula

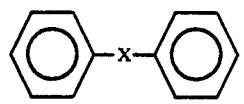

in which X is a bond, —O—, —S—, —SO$_2$—,

or an alkylidene group having 1 to 3 carbon atoms, provided that these skeletons may be substituted with a halogen atom or an alkyl group having 1 to 5 carbon atoms and that the total number of carbon atoms of each of $Ar^1$, $Ar^2$ and $Ar^3$ is not more than 20, $R^1$ and $R^2$ may be same or different and each independently represents a hydrogen atom or an alkyl group having 1 to 10 carbon atoms, q is a number of 0 to 20, and each of l, m and n is a number of 1 to 3.

2. A compound according to claim 1, wherein the (OH) —$Ar^1$— and $(OH)_n$—$Ar^3$— of the formula (I) may be same or different and are independently selected from the group consisting of monohydroxyphenyl, dihydroxyphenyl, monohydroxymonomethylphenyl, monohydroxynaphthyl, monochloromonohydroxyphenyl, dichloromonohydroxyphenyl, monobromomonohydroxyphenyl and dibromomonohydroxyphenyl.

3. A compound according to claim 1, wherein the $(OH)_m$—$Ar^2$< of the formula (I) is selected from the group consisting of monohydroxyphenylene, dihydroxyphenylene, monohydroxymonomethylphenylene, monohydroxynaphthylene, monochloromonohydroxyphenylene, dichloromonohydroxyphenylene, monobromomonohydroxyphenylene and dibromomonohydroxyphenylene.

4. A compound according to claim 1, wherein the $R^1$ and $R^2$ of the formula (I) may be same or different and are independently a hydrogen atom or methyl.

5. A compound according to claim 1, wherein the q in the formula (I) is a number of 0 to 5.

6. A process for the production of the compound of the formula (I) recited in claim 1, which comprises subjecting to a dehydration and condensation reaction an aldehyde compound of the formula (III)

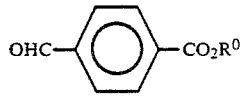
(III)

wherein $R^o$ is a hydrogen atom or an alkyl group having 1 to 10 carbon atoms and an aromatic hydroxy compound of the formula (IV)

$Ar^o$—$(OH)_u$  (IV)

wherein $Ar^o$ is a benzene skeleton, a naphthalene skeleton or a skeleton of the formula

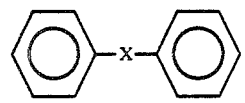

in which

X is a bond, —O—, —S—, —SO$_2$,

or an alkylidene group having 1 to 3 carbon atoms, provided that these skeletons may be substituted with a halogen atom or an alkyl group having 1 to 5 carbon atoms and that the total number of carbons of $Ar^o$ is not more than 20, and u is a number of 1 to 3, in the presence of an acidic catalyst, and optionally, then subjecting the reaction product to a hydrolysis reaction.

7. An epoxy compound of the formula (II)

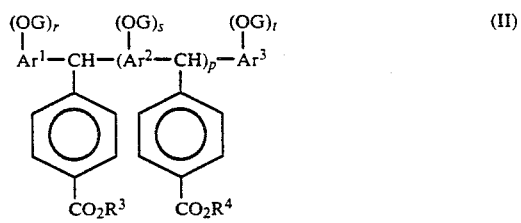

wherein:

$Ar^1$, $Ar^2$ and $Ar^3$ are as defined in the formula (I),

G is

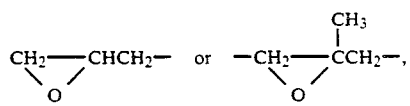

$R^3$ and $R^4$ may be same or different and each independently represents

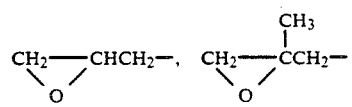

or an alkyl group having 1 to 10 carbon atoms, p is a number of 0 to 20, and r, s and t are independently a number of 1 to 3.

8. A compound according to claim 7, wherein the $(OG)_r$—$Ar^1$— and $(OG)_t$—$Ar^3$— of the formula (II) may be same or different and are independently selected from the group consisting of monoglycidyloxyphenyl, di(glycidyloxy)phenyl, monoglycidyloxymonomethylphenyl, monoglycidyloxynaphthyl, monochloromonoglycidyloxyphenyl, dichloromonoglycidyloxyphenyl, monobromomonoglycidyloxyphenyl and dibromomonoglycidyloxyphenyl.

9. A compound according to claim 7, wherein the $(OG)_s$—$Ar^2$< is selected from the group consisting of monoglycidyloxyphenylene, di(glycidyloxy)phenylene, monoglycidyloxymonomethylphenylene, monoglycidyloxynaphthylene, monochloromonoglycidyloxyphenylene, dichloromonoglycidyloxyphenylene, monobromomonoglycidyloxyphenylene and dibromomonoglycidyloxyphenylene.

10. A compound according to claim 7, wherein $R^3$ and $R^4$ of the formula (II) may be same or different and are independently

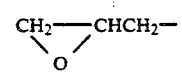

or methyl.

11. A compound according to claim 7, wherein p in the formula (II) is a number of 0 to 5.

12. A process for the production of the epoxy compound of the formula (II) recited in claim 7, which comprises reacting the compound of the formula (I) recited in claim 1 with a halohydrin selected from epihalohydrins and β-methylepihalohydrins;
   (i) at one step in the presence of an basic compound, or
   (ii) first in the presence of a quaternary ammonium salt and then in the presence of a basic compound.

13. A process for the production of the compound of the formula (II) which comprises:
   (1) subjecting a dehydration and condensation reaction an aldehyde compound of the formula (III)-1,

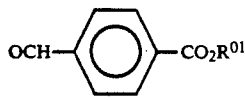

wherein $R^{01}$ is an alkyl group having 1 to 10 carbon atoms, and an aromatic hydroxy compound of the formula (IV) cited in claim 6 in the presence of an acidic catalyst,
   (2) subjecting the resultant reaction mixture to a hydrolysis reaction in the presence of a basic compound, and
   (3) adding an halohydrin selected from epihalohydrins and β-methylepihalohydrins to the resultant hydrolysis reaction mixture to react a hydrolysis reaction product in said mixture with the halohydrin.

14. A method of using the compound of the formula (I)

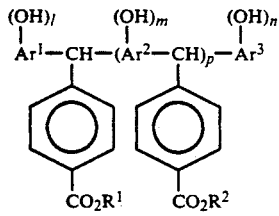

wherein:
   $Ar^1$, $Ar^2$ and $Ar^3$ may be the same or different and each independently represents a benzene skeleton, a naphthalene skeleton or a skeleton of the formula

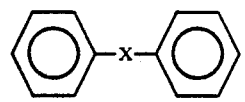

in which X is a bond, —O—, —S—, —SO$_2$—,

or alkylidene group having 1 to 3 carbon atoms, provided that these skeletons may be substituted with a halogen atom or an alkyl group having 1 to 5 carbon atoms and that the total number of carbon atoms of each of $Ar^1$, $Ar^2$ and $Ar^3$ is not more than 20,
   $R^1$ and $R^2$ may be the same or different and each independently represents a hydrogen atom or an alkyl group having 1 to 10 carbon atoms,
   q is a number of 0 to 20, and
   each of l, m and n is a number of 1 to 3, as a curing agent, comprising adding the compound of formula I to a thermosetting resin to form a cured product.

15. A molded cured product of a thermosetting resin comprising the epoxy compound of the formula (II)

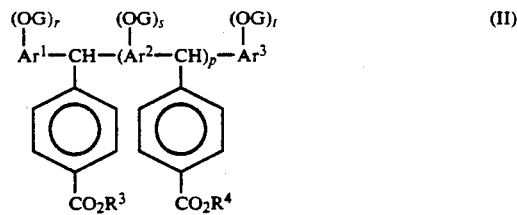

wherein:
   $Ar^1$, $Ar^2$ and $Ar^3$ are as defined in the formula (I),

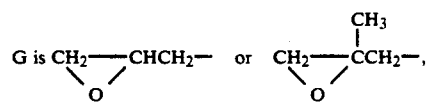

$R^3$ and $R^4$ may be the same or different and each independently represents

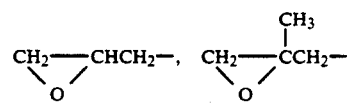

or an alkyl group having 1 to 10 carbon atoms,
   p is a number of 0 to 20, and
   r, s and t are independently a number of 1 to 3.

16. A composite material comprising a matrix resin of a cured product of a thermosetting resin comprising the epoxy compound of the formula (II)

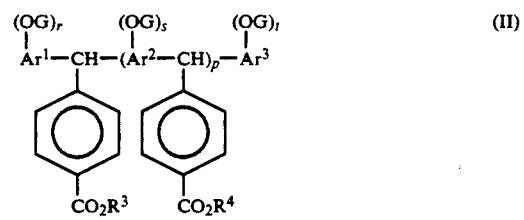

wherein:
   $Ar^1$, $Ar^2$ and $Ar^3$ are as defined in the formula (I),

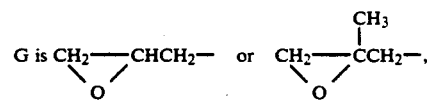

$R^3$ and $R^4$ may be the same or different and each independently represents

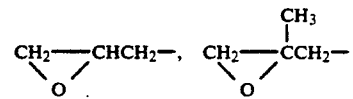

or an alkyl group having 1 to 10 carbon atoms,
   p is a number of 0 to 20, and
   r, s and t are independently a number of 1 to 3, and a reinforcing material.

17. A composite material according to claim 16, wherein the reinforcing material is a carbon fiber, an aramide fiber or a glass fiber.

* * * * *